(12) United States Patent
Kirollos

(10) Patent No.: US 11,103,661 B2
(45) Date of Patent: Aug. 31, 2021

(54) APPARATUS AND METHOD FOR ADAPTIVE RAMPED CONTROL OF POSITIVE AIRWAY PRESSURE (PAP)

(71) Applicant: ResMed Pty Ltd, Bella Vista (AU)

(72) Inventor: Mina Samir Kirollos, Sydney (AU)

(73) Assignee: ResMed Pty Ltd

( * ) Notice: Subject to any disclaimer, the term of this patent is extended or adjusted under 35 U.S.C. 154(b) by 507 days.

(21) Appl. No.: 15/703,186

(22) Filed: Sep. 13, 2017

(65) Prior Publication Data

US 2018/0071471 A1    Mar. 15, 2018

(30) Foreign Application Priority Data

Sep. 14, 2016  (AU) ................. 2016903685

(51) Int. Cl.
*A61M 16/00*    (2006.01)

(52) U.S. Cl.
CPC ...... *A61M 16/026* (2017.08); *A61M 16/0069* (2014.02); *A61M 2016/0027* (2013.01); *A61M 2016/0036* (2013.01); *A61M 2205/15* (2013.01); *A61M 2205/3303* (2013.01); *A61M 2205/3344* (2013.01); *A61M 2205/3365* (2013.01);
(Continued)

(58) Field of Classification Search
CPC ............ A61M 16/026; A61M 16/0069; A61M 2205/42; A61M 2205/3584; A61M 2016/0036; A61M 2205/3365; A61M 2205/52; A61M 2205/15; A61M 2205/3303; A61M 2205/3344; A61M 2205/505; A61M 2016/0027;
(Continued)

(56) References Cited

U.S. PATENT DOCUMENTS

| 4,944,310 A | 7/1990 | Sullivan |
| 6,532,959 B1 | 3/2003 | Berthon-Jones |

(Continued)

FOREIGN PATENT DOCUMENTS

| WO | 2011006199 A1 | 1/2011 |
| WO | 2014015238 A1 | 1/2014 |

(Continued)

*Primary Examiner* — Victoria Murphy
*Assistant Examiner* — Arielle Wolff
(74) *Attorney, Agent, or Firm* — Botos Churchill IP Law LLP

(57) ABSTRACT

Methods and/or apparatus automate setting of a pressure ramp to permit pressure to gradually arrive at a treatment pressure such as in the initial or pre-sleep stages of use of a respiratory therapy pressure device for treatment of a respiratory disorder during sleep (e.g., sleep disordered breathing). In an example, apparatus for treating a respiratory disorder may include a breathable gas pressure generating device. The apparatus may include a controller, including a processor(s). The controller may be configured to collect historic sleep onset parameter(s) concerning timing of a patient falling asleep. The apparatus may determine, based on the historic sleep onset parameter(s), a pre-sleep limit. The apparatus may determine a pre-sleep profile of pressure versus time having a duration spanning the pre-sleep limit and having a plurality of ramping sub-therapeutic pressures. The apparatus may control, upon initiation of treatment, setting of the pressure generating device according to the pre-sleep profile.

16 Claims, 16 Drawing Sheets

(52) U.S. Cl.
CPC . *A61M 2205/3584* (2013.01); *A61M 2205/42* (2013.01); *A61M 2205/505* (2013.01); *A61M 2205/52* (2013.01)

(58) Field of Classification Search
CPC .... A61M 21/02; A61B 5/4806; A61B 5/4809; A61B 5/4812
See application file for complete search history.

(56) References Cited

U.S. PATENT DOCUMENTS

| | | |
|---|---|---|
| 7,500,481 B2 | 3/2009 | Delache et al. |
| 2006/0102179 A1 | 5/2006 | Rapoport et al. |
| 2009/0038616 A1* | 2/2009 | Mulcahy ............. A61M 16/024 128/204.23 |
| 2011/0230790 A1* | 9/2011 | Kozlov ................ A61B 5/4812 600/595 |
| 2012/0179061 A1* | 7/2012 | Ramanan ............ A61M 16/024 600/538 |
| 2017/0238867 A1* | 8/2017 | Javed .................... A61B 5/486 |

FOREIGN PATENT DOCUMENTS

| | | |
|---|---|---|
| WO | 2015006364 A2 | 1/2015 |
| WO | 2015131219 A1 | 9/2015 |
| WO | 2017029284 A1 | 2/2017 |

\* cited by examiner

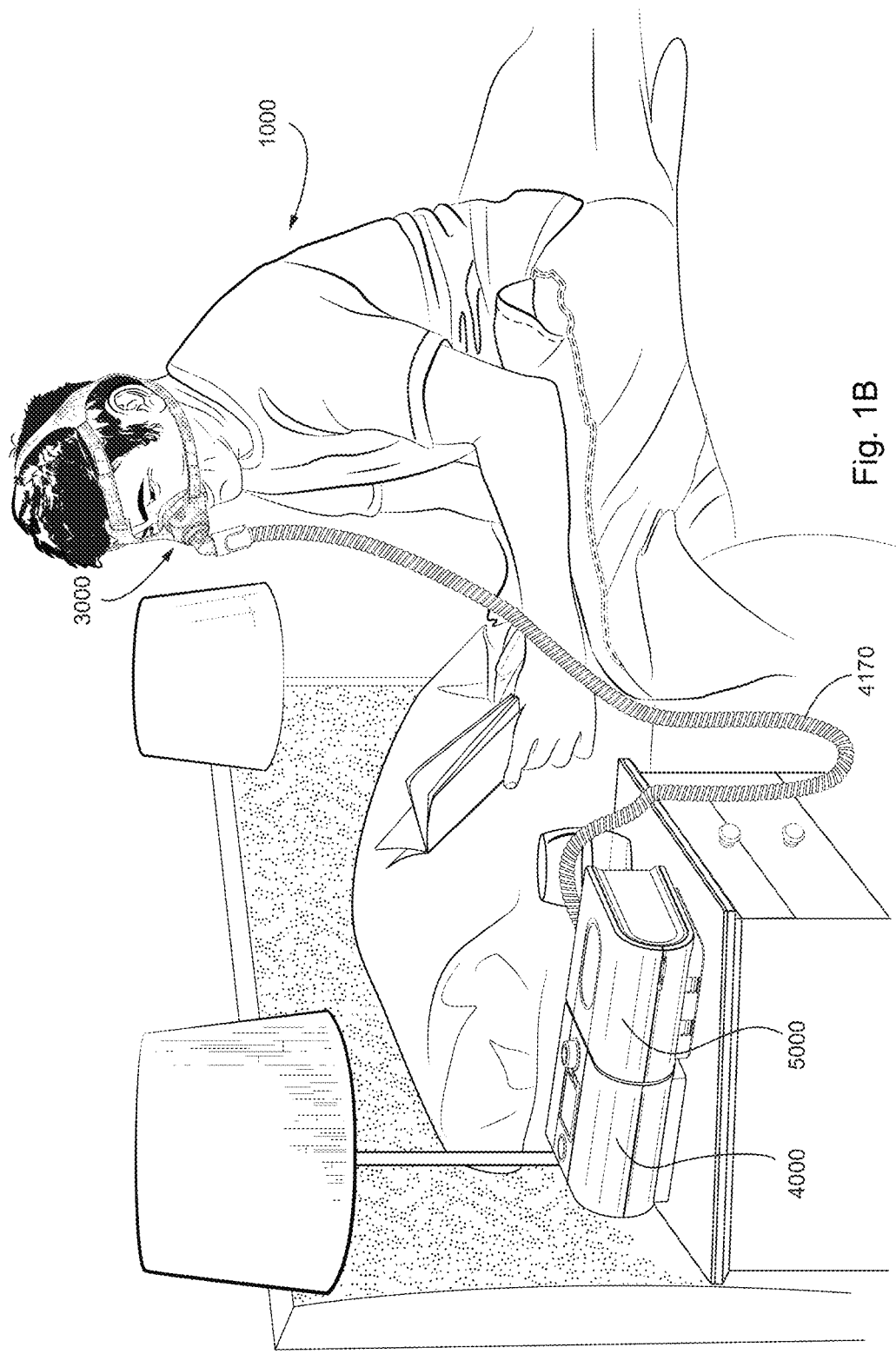

APPARATUS AND METHOD FOR ADAPTIVE RAMPED CONTROL OF POSITIVE AIRWAY PRESSURE (PAP)

1 CROSS-REFERENCE TO RELATED APPLICATIONS

The present application claims priority from Australian Provisional Patent Application Number AU 2016903685, filed on Sep. 14, 2016, the entire contents of which is incorporated herein by reference.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE INVENTION

5.1 Field of the Invention

The present technology relates to one or more of the detection, diagnosis, treatment, prevention and amelioration of respiratory-related disorders. In particular, the present technology relates to medical devices or apparatus, and their use.

5.2 Description of the Related Art 5.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 second duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

5.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilator support to a patient through the upper airways to assist the patient in taking a full breath and/or maintain adequate oxygen levels in the body by doing some or all of the work of breathing. The ventilator support is provided via a patient interface. NIV has been used to treat CSR, OHS, COPD, NMD, and Chest Wall disorders.

5.2.3 Systems

One known device for providing CPAP therapy (PAP device) is the S9 Sleep Therapy System, manufactured by ResMed. Ventilators such as the ResMed Stellar™ Series of Adult and Paediatric Ventilators may provide support for non-invasive non-dependent ventilation for a range of patients for treating a number of conditions such as but not limited to CSR, NMD, OHS and COPD.

A system may comprise a PAP Device/ventilator, an air circuit, a humidifier, a patient interface, and data management.

5.2.4 Patient Interface

A patient interface may be used to interface respiratory equipment to its user, for example by providing a flow of air. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cm $H_2O$. For other forms of therapy, such as the delivery of oxygen, the patient interface may not include a seal sufficient to facilitate delivery to the airways of a supply of gas at a positive pressure of about 10 cm $H_2O$.

5.2.5 Respiratory Apparatus (PAP Device/Ventilator)

Examples of respiratory apparatus include ResMed's S9 AutoSet™ PAP device and ResMed's Stellar™ 150 ventilator. PAP devices or ventilators typically comprise a pressure device, such as a motor-driven blower or a compressed gas reservoir, and are configured to supply a flow of air to the airway of a patient. In some cases, the flow of air may be supplied to the airway of the patient at positive pressure. The outlet of the PAP device or the ventilator is connected via an air circuit to a patient interface such as those described above.

6 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

A further aspect of the present technology relates to systems used in the diagnosis, amelioration, treatment or prevention of a respiratory disorder.

Some versions of the present technology include methods and/or apparatus for automated setting of timing of a ramp for pressure to permit the pressure to gradually arrive at a treatment pressure such as in the initial or pre-sleep stages of use of a respiratory therapy pressure device that may be used for treatment of a respiratory disorder during sleep (e.g., sleep disordered breathing).

Some versions of the present technology include apparatus(es) for treating a respiratory disorder. The apparatus may include a breathable gas pressure generating device. The apparatus may include a controller, including at least one processor. The controller may be configured to collect one or more historic sleep onset parameters concerning timing of a patient falling asleep. The controller may be configured to determine, based on the one or more historic sleep onset parameters, a pre-sleep limit. The controller may be configured to determine a pre-sleep profile of pressure versus time having a duration spanning the pre-sleep limit and having a plurality of ramping sub-therapeutic pressures. The controller may be configured to control, upon initiation of treatment, setting of the breathable gas pressure generating device according to the pre-sleep profile of pressure versus time.

The controller may be configured to collect the one or more historic sleep onset parameters by detecting, with one or more sensors, sleep onset of the patient during use of the breathable gas pressure generating device. The controller may be configured to collect the one or more historic sleep onset parameters by determining a length of time for the sleep onset of the patient. The controller may be configured to collect the one or more historic sleep onset parameters by receiving a sleep onset time at a user input device. The controller may be configured to calculate the pre-sleep limit as a function of any one of: a maximum of a plurality of the historic sleep onset parameters; a mean of a plurality of the historic sleep onset parameters; and a percentile of the one or more historic sleep onset parameters.

The controller may be configured to calculate the pre-sleep limit from a percentile of a plurality of the historic sleep onset parameters, and wherein the pre-sleep limit may be calculated as a percentage of the percentile. The controller may be configured to collect a plurality of the historic sleep onset parameters according to a window timeframe comprising a number of treatment sessions. The window timeframe may be a rolling window timeframe. The controller may be further configured to set a default pre-sleep limit in an absence of a sufficient collection of one or more historic sleep onset parameters.

The controller may be configured to control a display to provide a prompt for input, the prompt for input including: one or both of (a) at least one of the one or more historic sleep onset parameters, and (b) at least one calculated statistic concerning the one or more historic sleep onset parameters. The controller may be configured to determine the pre-sleep limit based on input received in response to the prompt.

In some versions, the pre-sleep profile may start delivered pressure at a first pressure and may end at a minimum therapeutic pressure. The minimum therapeutic pressure may be higher than the first pressure.

Some versions of the present technology include a method(s) for controlling a pressure treatment for a respiratory disorder. The method may include generating a flow of breathable gas at a pressure above atmospheric pressure with a pressure generating device. The method may include, such as in one or more controllers: collecting one or more historic sleep onset parameters concerning timing of a patient falling asleep; determining, based on the one or more historic sleep onset parameters, a pre-sleep limit; determining a pre-sleep profile of pressure versus time having a duration spanning the pre-sleep limit and having a plurality of ramping sub-therapeutic pressures; and/or controlling, upon initiation of treatment, setting of the flow of breathable gas according to the pre-sleep profile of pressure versus time.

The method may include, such as in the one or more controllers, collecting the one or more historic sleep onset parameters by detecting, with one or more sensors, sleep onset of the patient during use of the breathable gas pressure generating device; and determining a length of time for the sleep onset of the patient. The collecting of the one or more historic sleep onset parameters may include receiving a sleep onset time at a user input device. The method may include, such as in one or more controllers, calculating the pre-sleep limit as a function of any one of: a maximum of a plurality of the historic sleep onset parameters; a mean of a plurality of the historic sleep onset parameters; and a percentile of the one or more historic sleep onset parameters. The method may include, such as in one or more controllers, calculating the pre-sleep limit from a percentile of a plurality of the historic sleep onset parameters, wherein the pre-sleep limit is calculated as a percentage of the percentile. The method may include, such as in one or more controllers, collecting a plurality of the historic sleep onset parameters according to a window timeframe comprising a number of treatment sessions. The window timeframe may be a rolling window timeframe.

In some versions, the method may include, such as in one or more controllers, setting a default pre-sleep limit in an absence of a sufficient collection of one or more historic sleep onset parameters. The method may include, such as in the one or more controllers: controlling a display to provide a prompt for input, the prompt for input including: one or both of (a) at least one of the one or more historic sleep onset parameters, and (b) at least one calculated statistic concerning the one or more historic sleep onset parameters; and determining the pre-sleep limit based on input received in response to the prompt. The pre-sleep profile may start delivered pressure at a first pressure and may end at a minimum therapeutic pressure, the minimum therapeutic pressure being higher than the first pressure.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7 BRIEF DESCRIPTION OF THE DRAWINGS

The present technology is illustrated by way of example, and not by way of limitation, in the figures of the accompanying drawings, in which like reference numerals refer to similar elements including:

7.1 Treatment Systems

FIG. 1A shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000.

7.2 Respiratory System

Figure 1A:
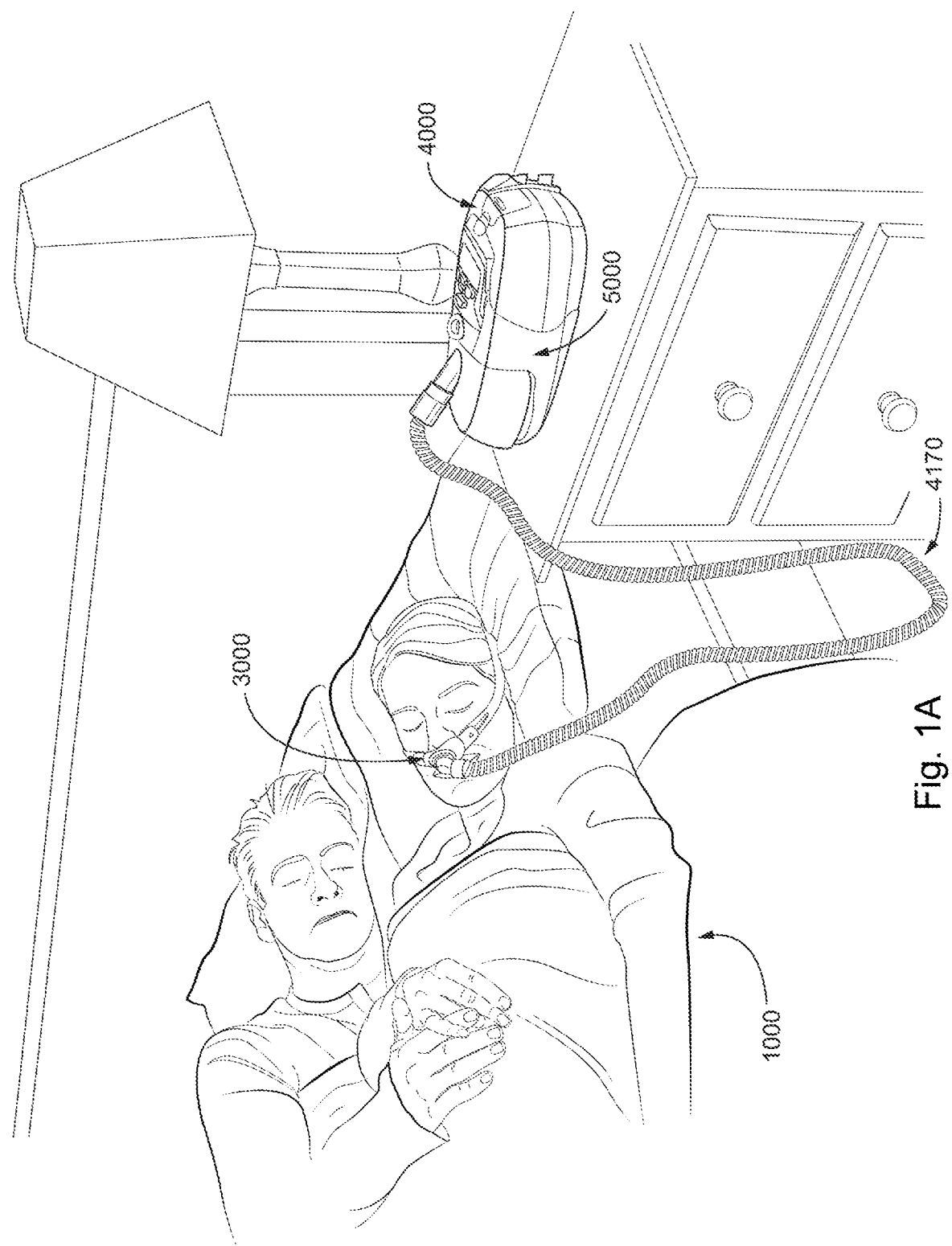
FIG. 1B shows a PAP device 4000 in use on a patient 1000 with a nasal mask 3000.
FIG. 1C shows a PAP device 4000 in use on a patient 1000 with a full-face mask 3000.
Figure 1C:
Figure 2A:
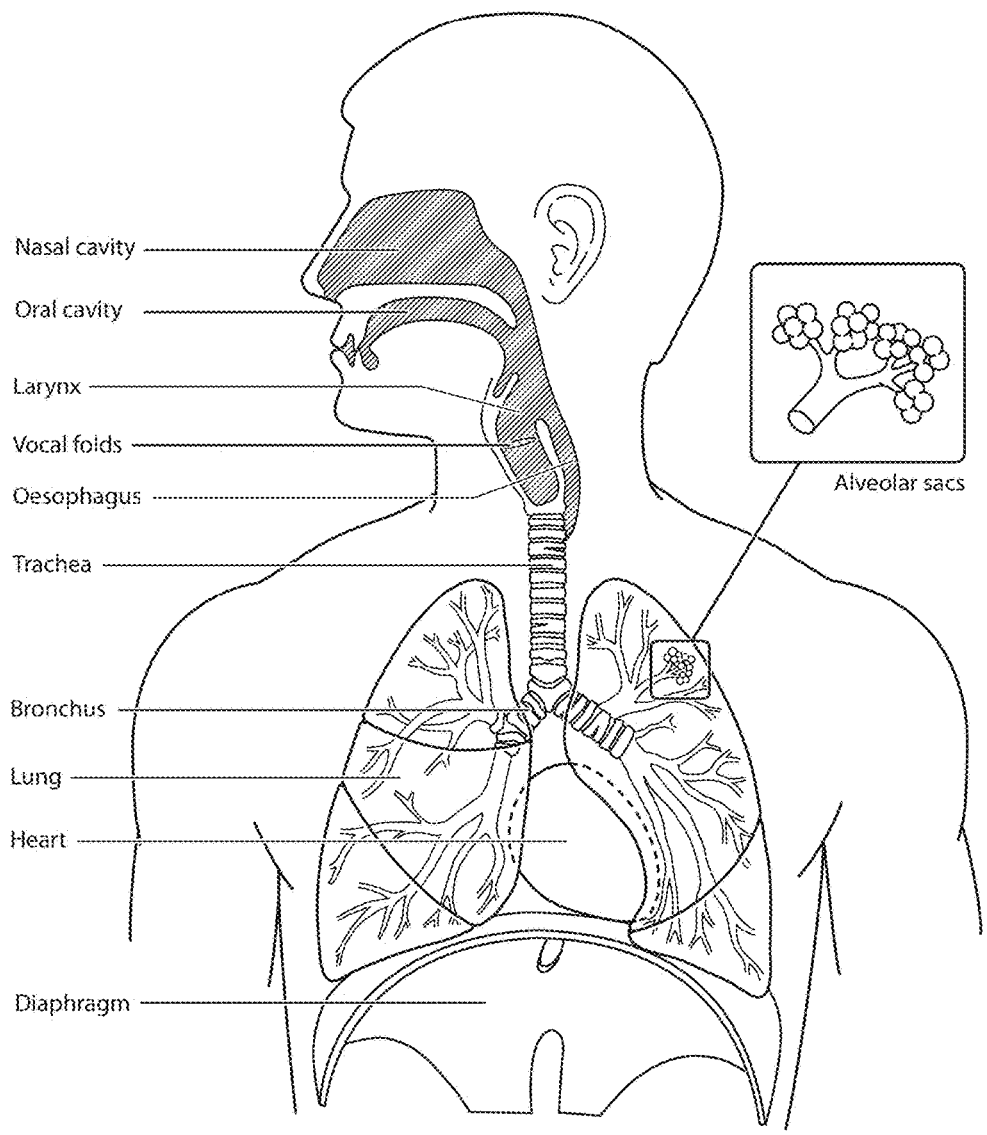

FIG. 2A shows an overview of a human respiratory system including the nasal and oral cavities, the larynx, vocal folds, oesophagus, trachea, bronchus, lung, alveolar sacs, heart and diaphragm.

Figure 2B:
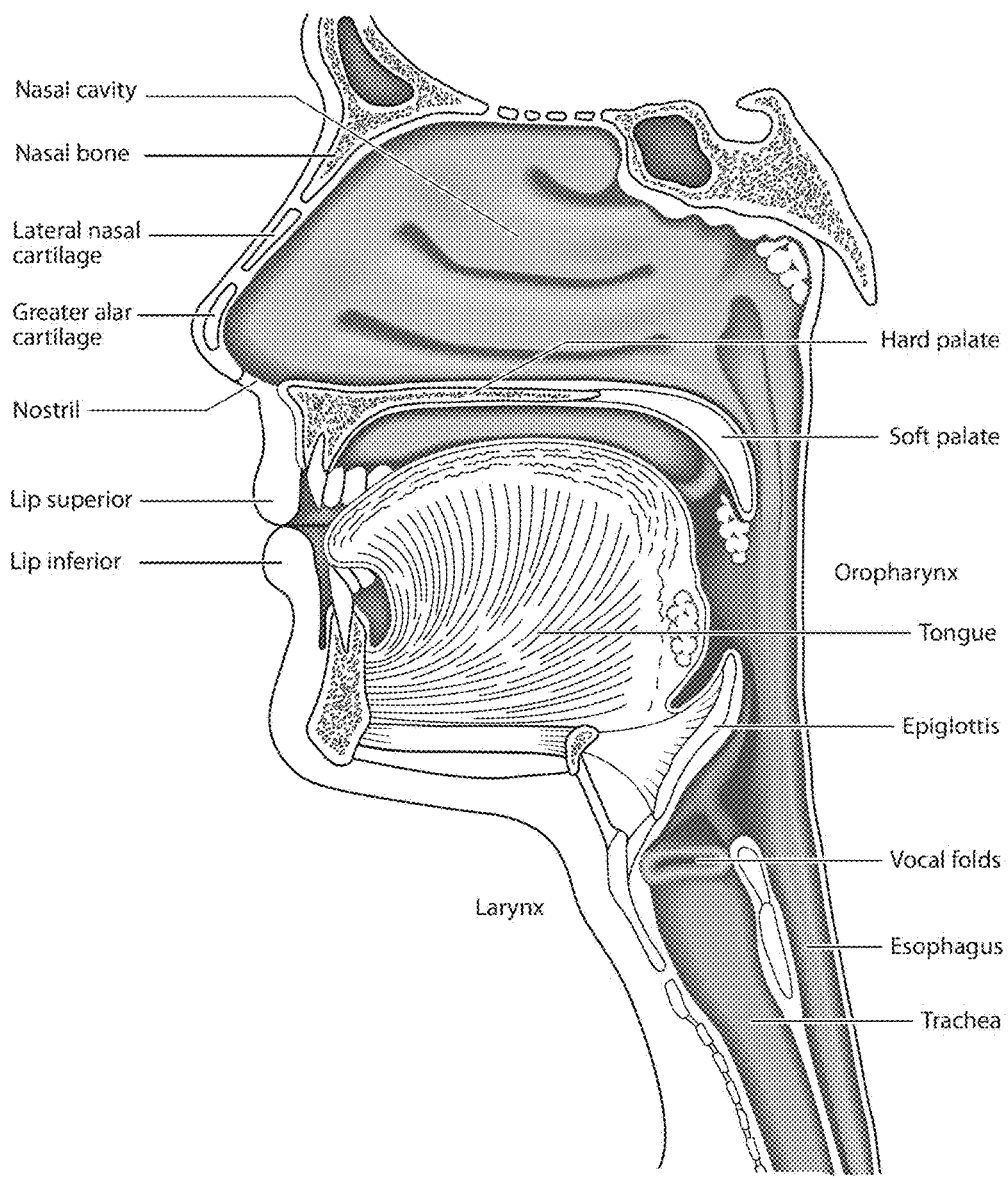

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

7.3 Patient Interface

Figure 3:
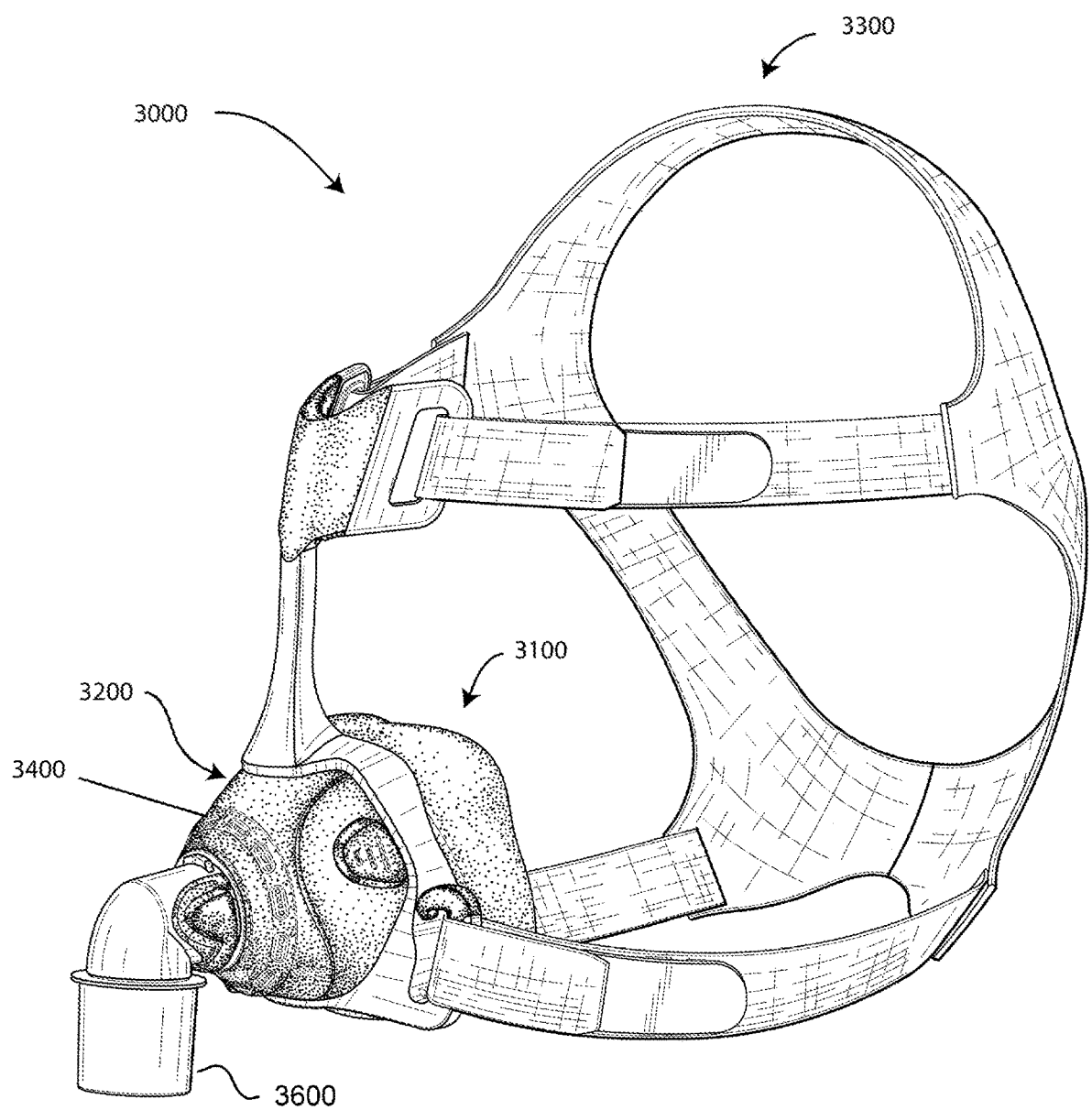

FIG. 3 shows a patient interface 3000 in accordance with one form of the present technology.

7.4 PAP Device

Figure 4A:
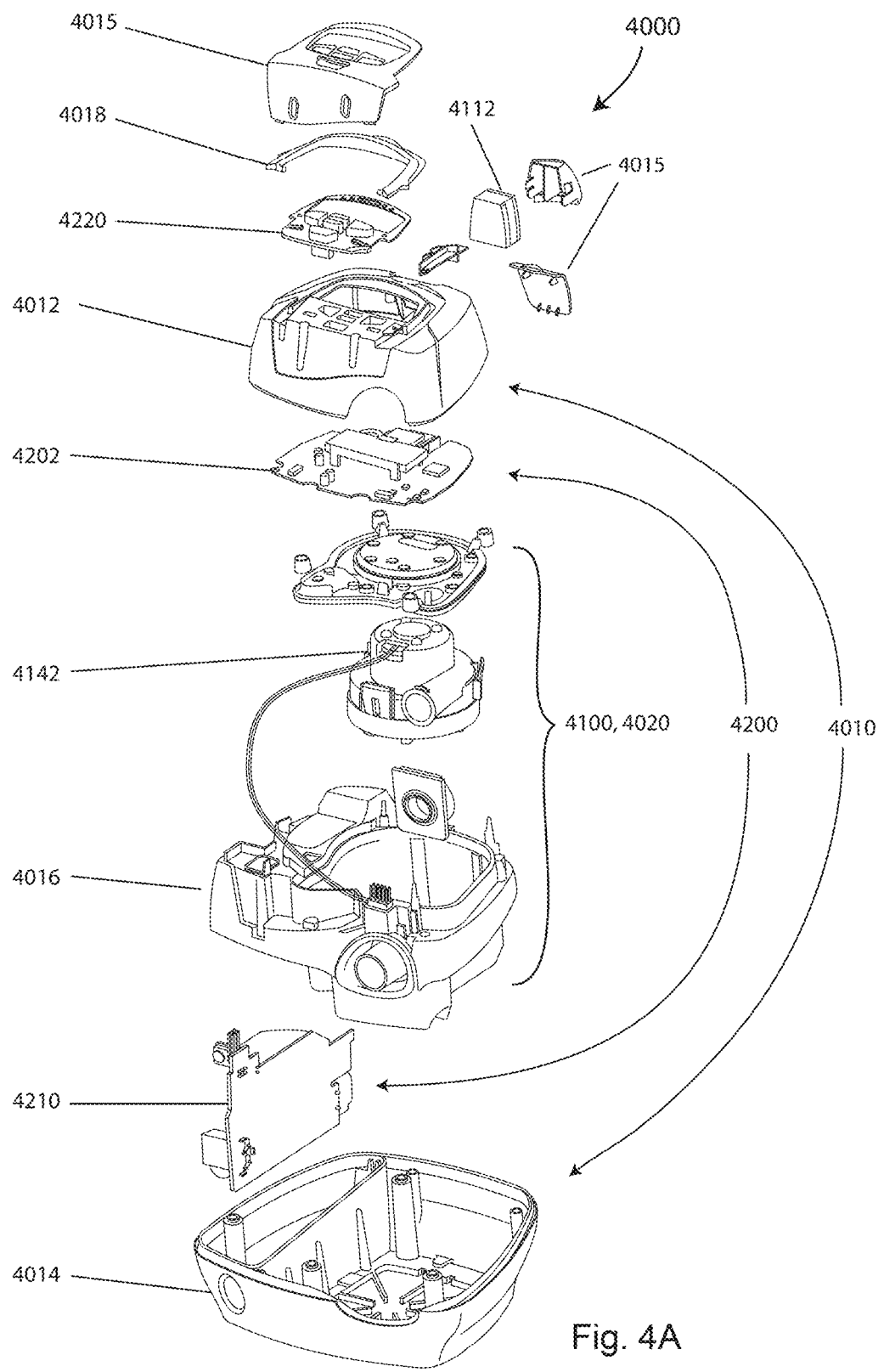

FIG. 4A shows a PAP device 4000 in accordance with one form of the present technology.

Figure 4B:
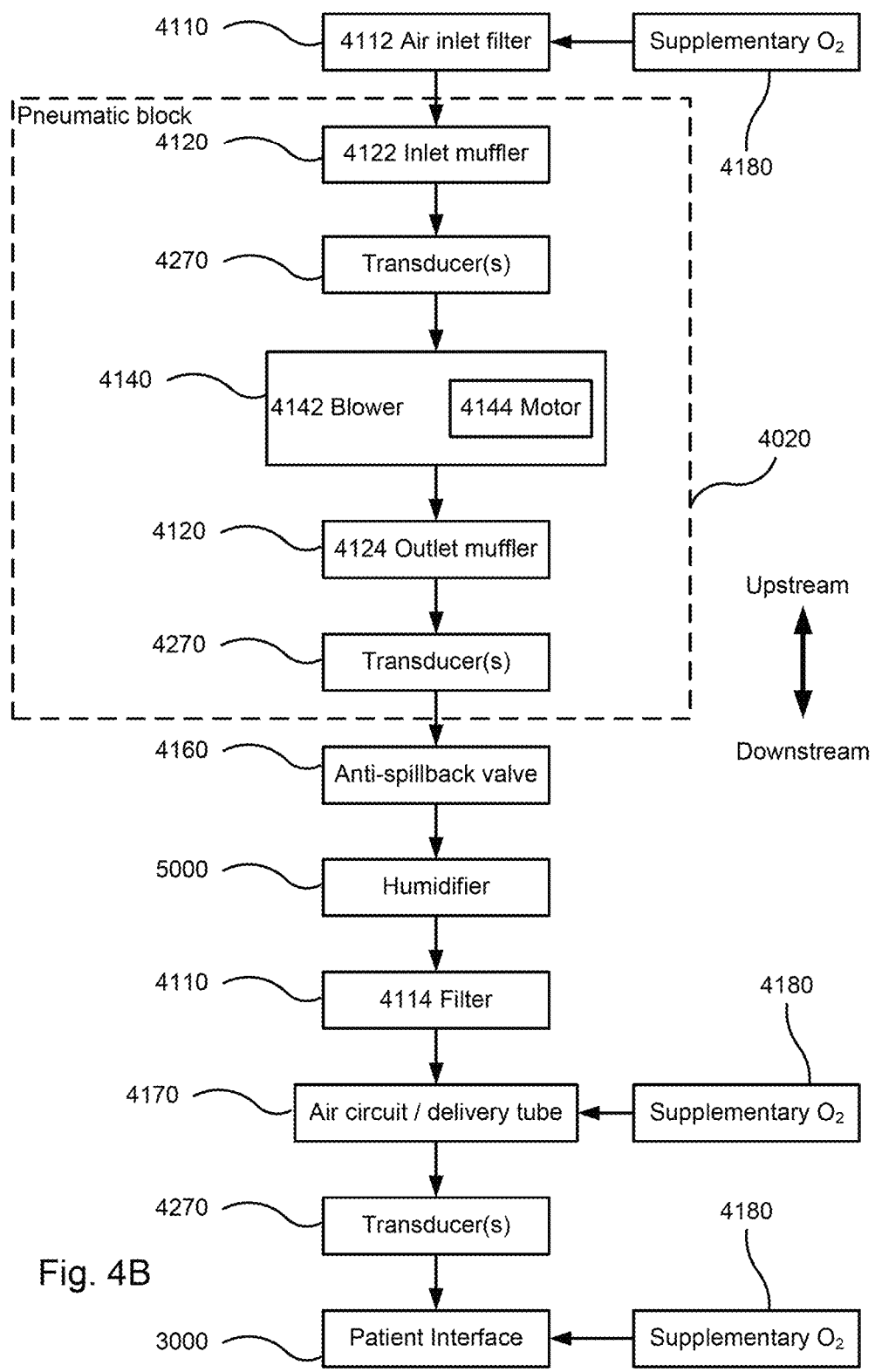

FIG. 4B shows a schematic diagram of the pneumatic circuit of a PAP device 4000 in accordance with one form of the present technology. The directions of upstream and downstream are indicated.

Figure 4C:
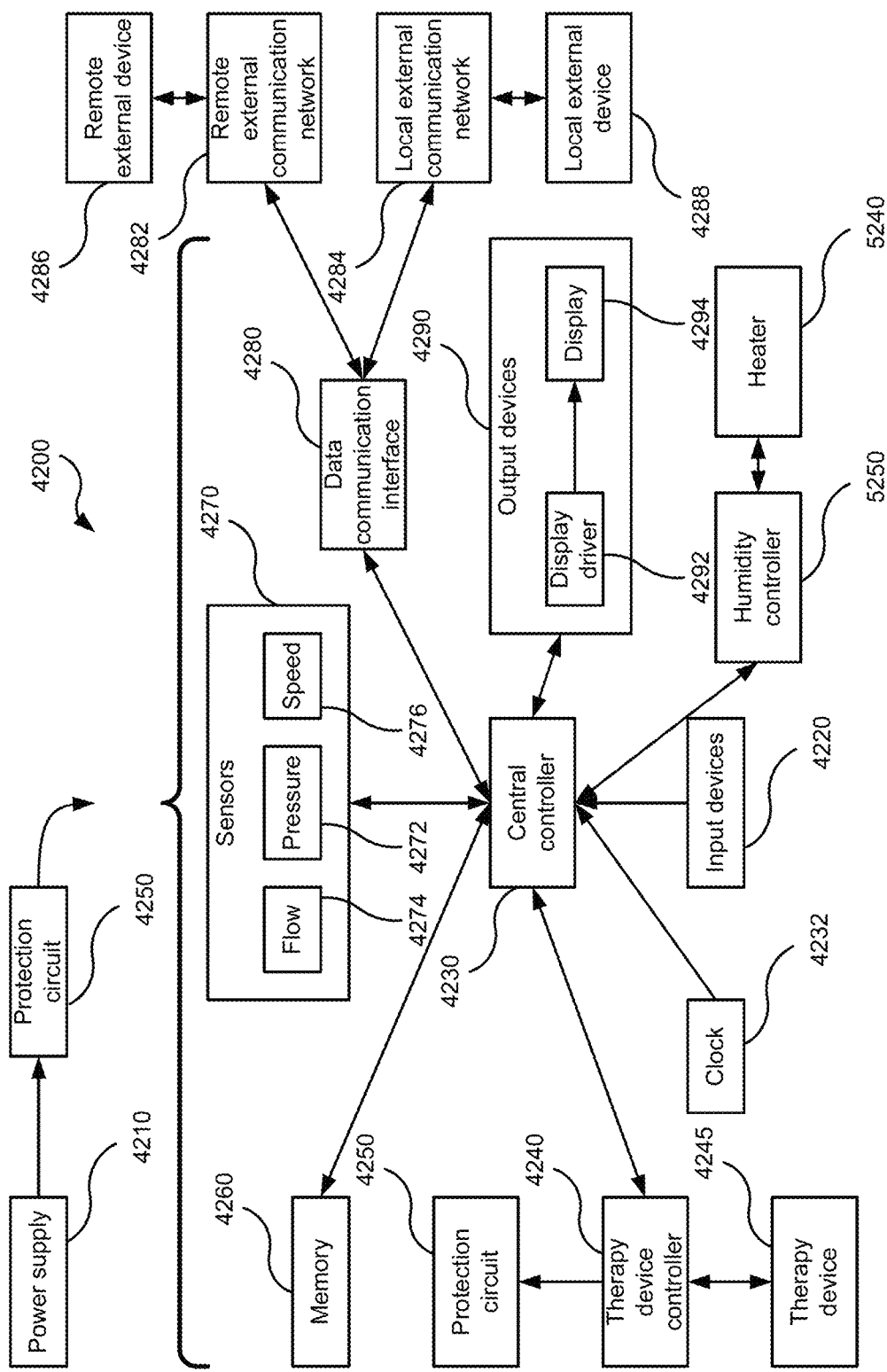

FIG. 4C shows a schematic diagram of the electrical components of a PAP device 4000 in accordance with one aspect of the present technology.

Figure 4D:
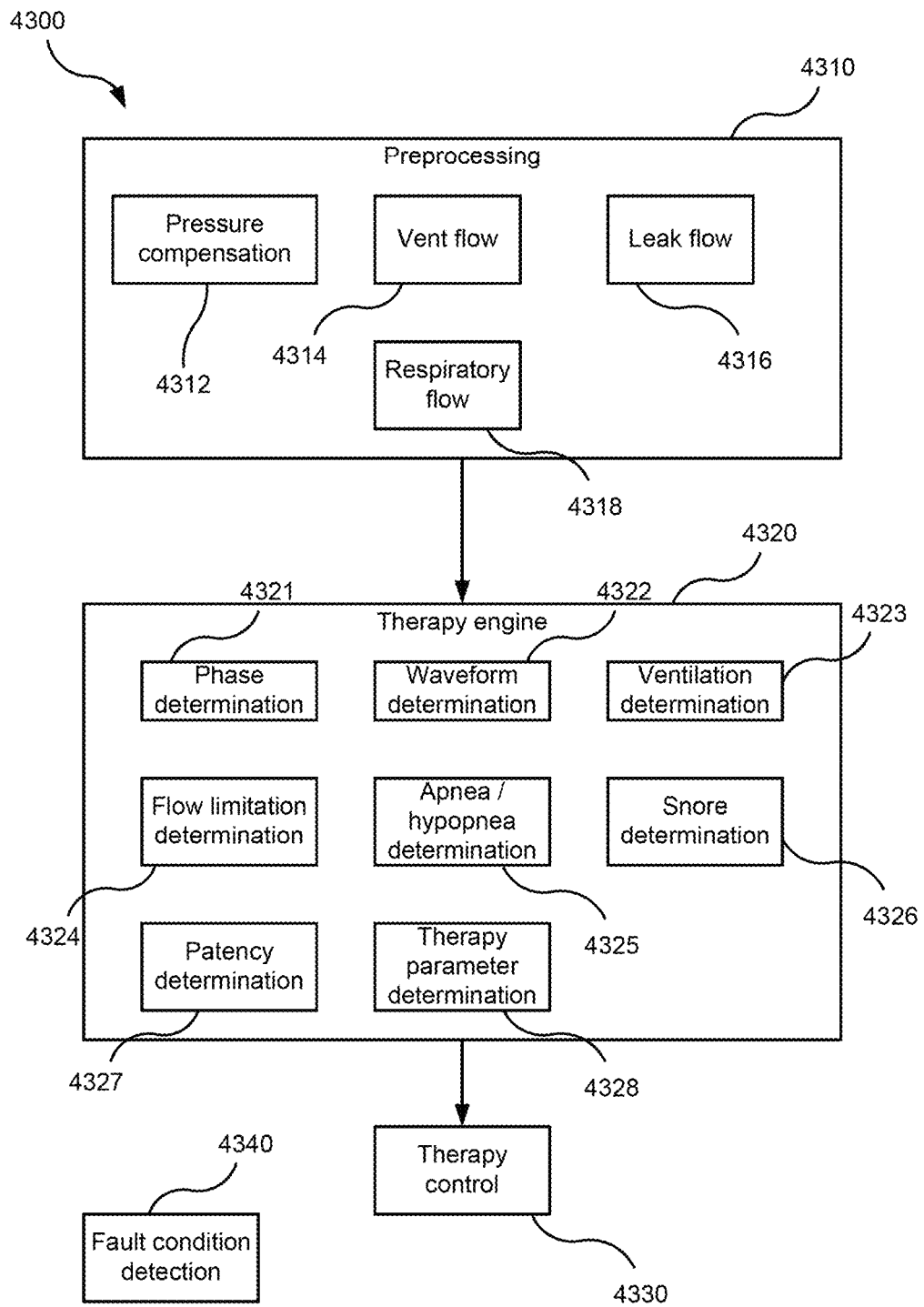

FIG. 4D shows a schematic diagram of the algorithms 4300 implemented in a PAP device 4000 in accordance with an aspect of the present technology. In this figure, arrows with solid lines indicate an actual flow of information, for example via an electronic signal.

Figure 4E:
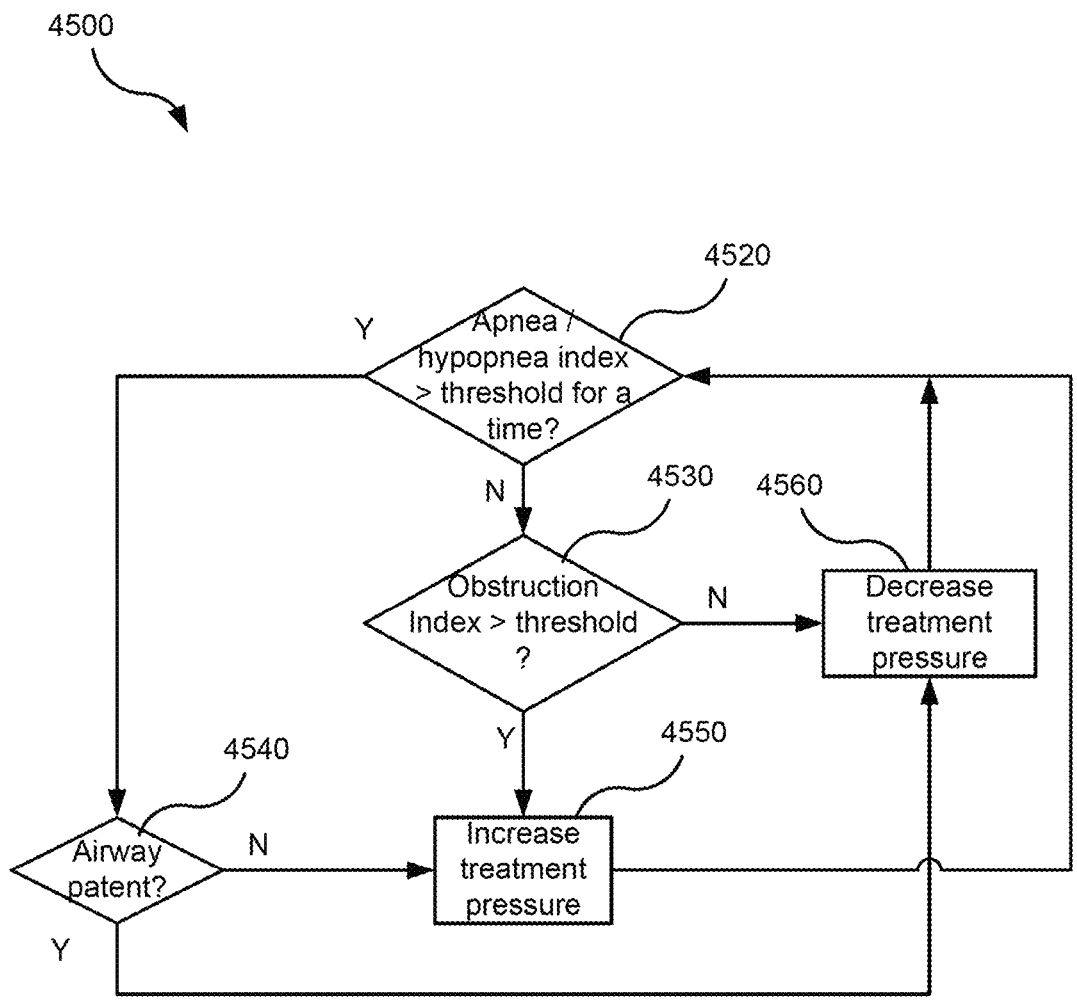

FIG. 4E is a flow chart illustrating a method 4500 carried out by the therapy engine module 4320 of FIG. 4D in accordance with one aspect of the present technology.

Figure 4F:
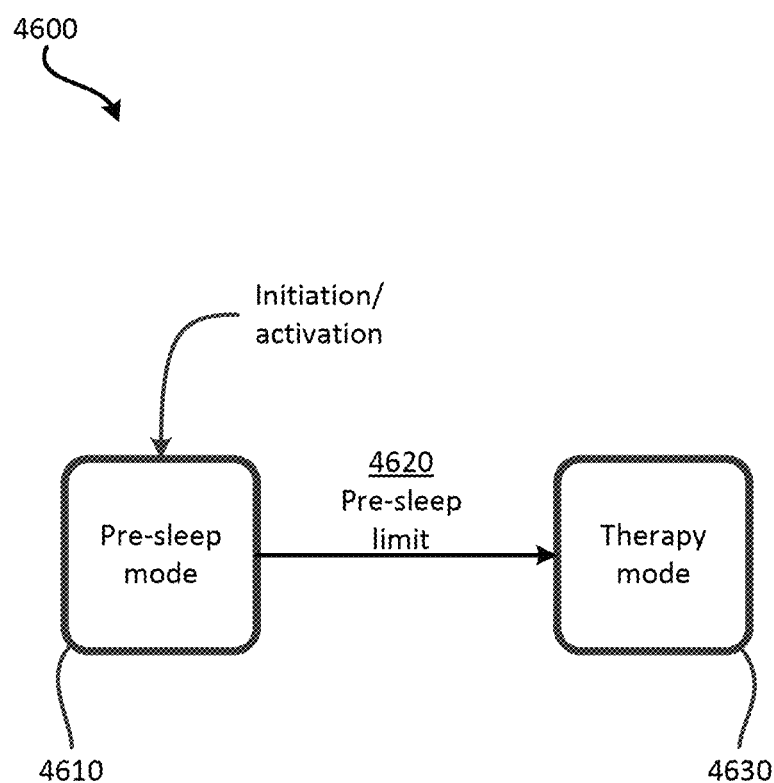

FIG. 4F is a state diagram illustrating an initial phase of operation of the therapy engine module 4320 of FIG. 4D in accordance with an aspect of the present technology.

Figure 4G:
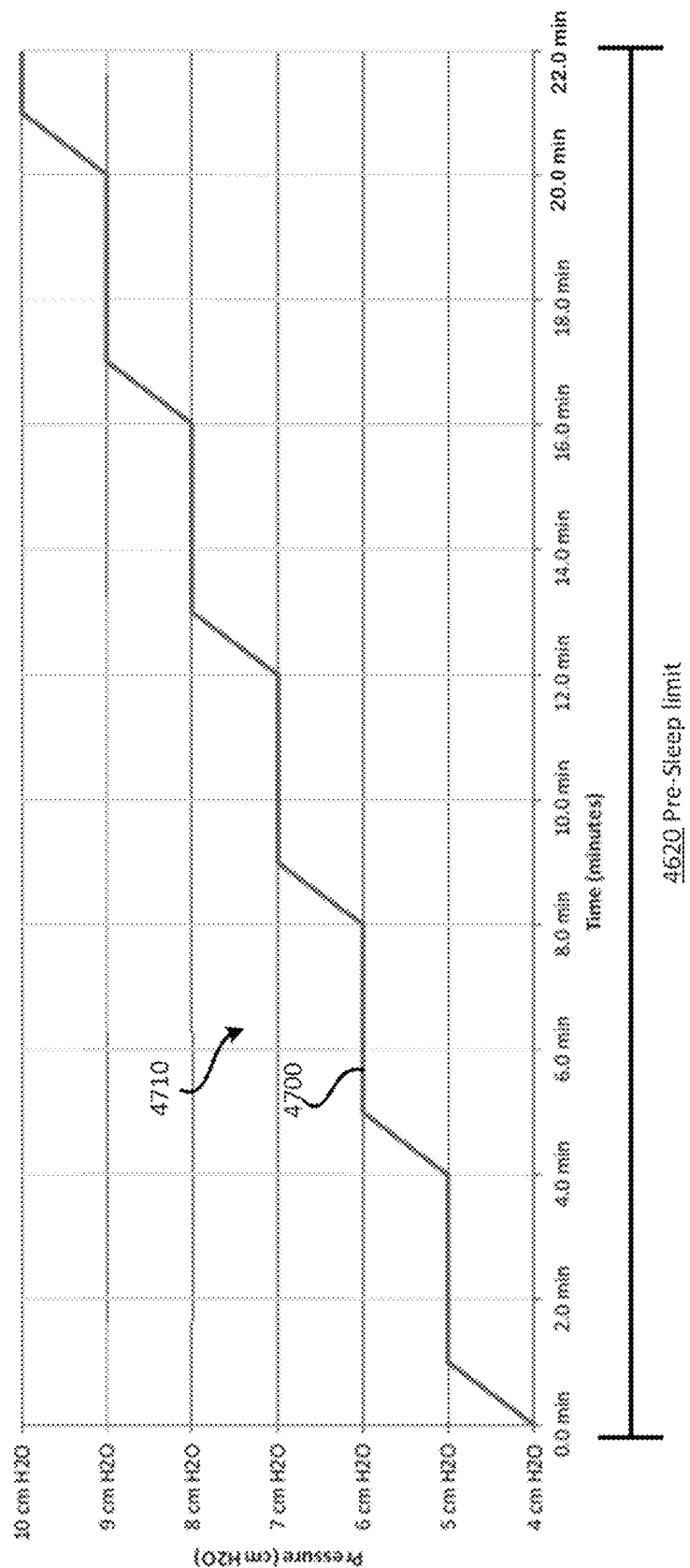
Figure 4H:
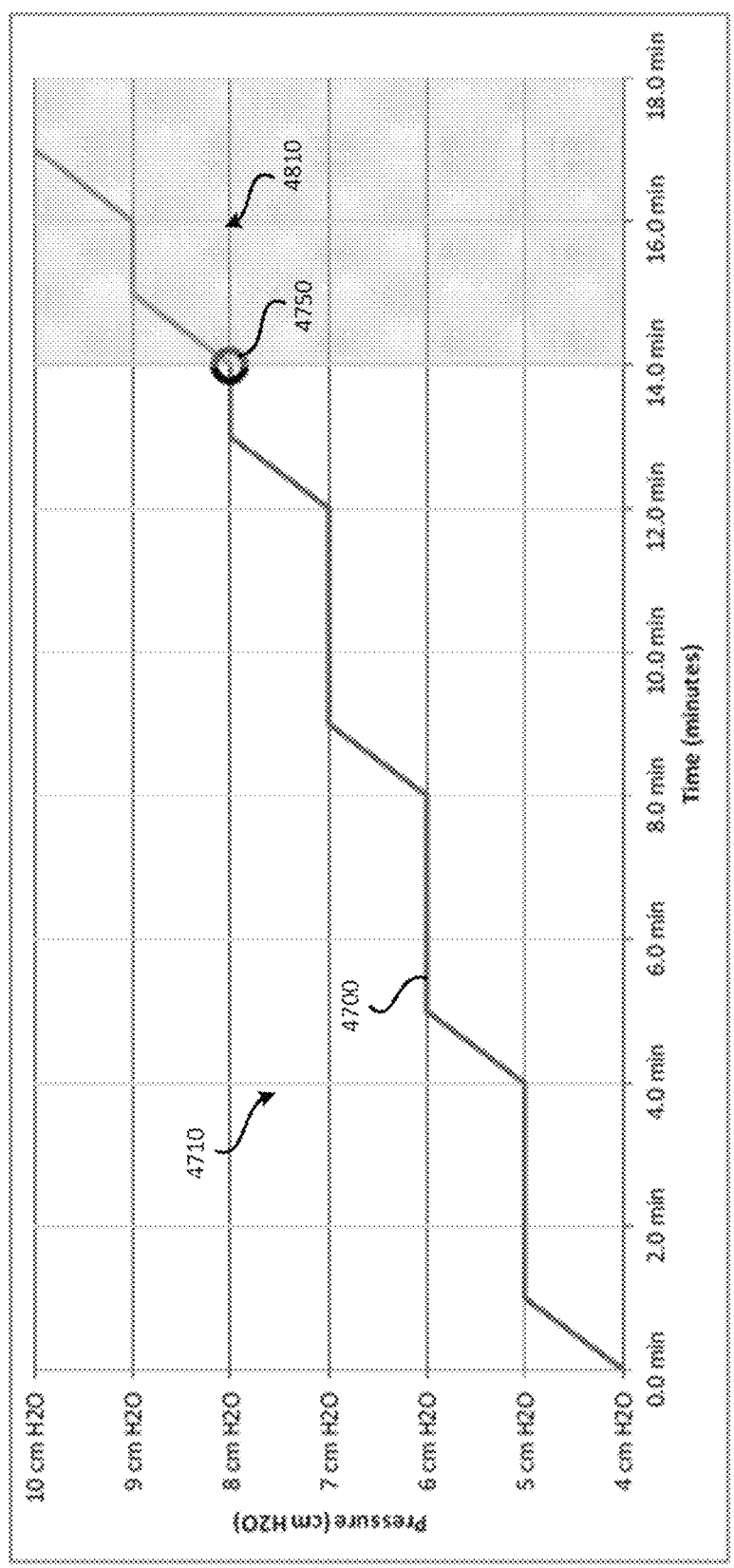

FIGS. 4G and 4H depict graphs illustrating the initial phase of operation of the therapy engine module 4320 of FIG. 4D as described with reference to FIG. 4F.

7.5 Humidifier

Figure 5:
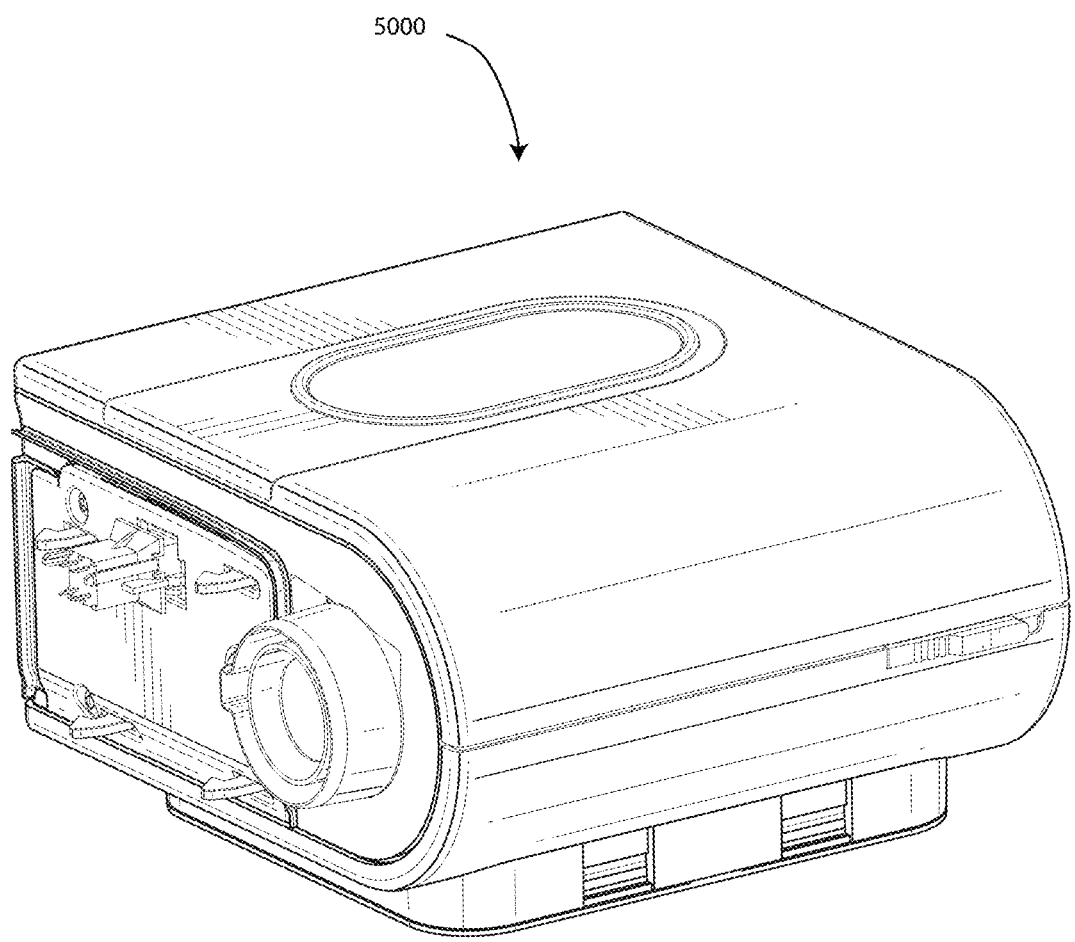

FIG. 5 shows a humidifier 5000 in accordance with one aspect of the present technology.

7.6 Breathing Waveforms

Figure 6:
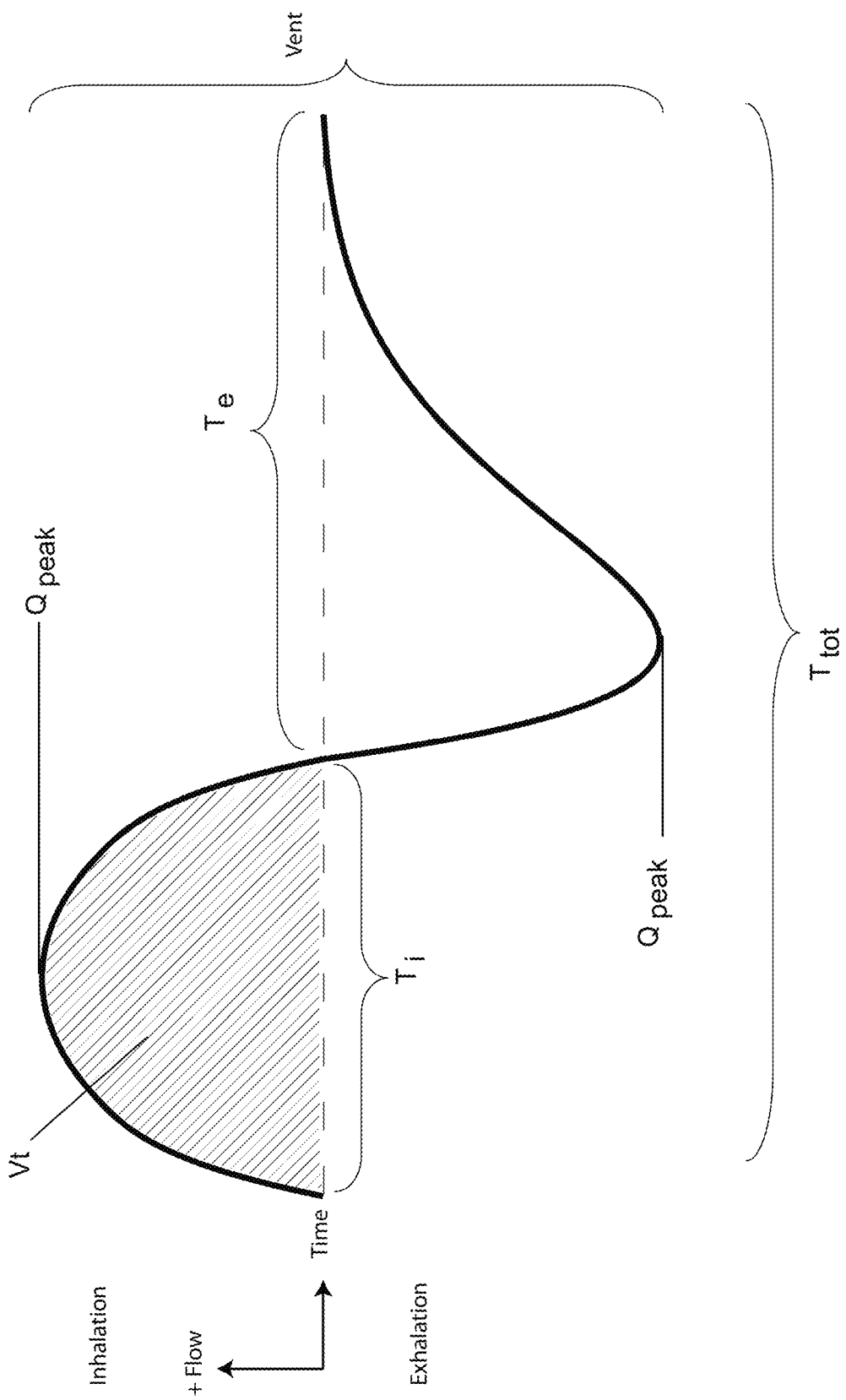

FIG. 6 shows a model typical breath waveform of a person while sleeping. The horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

8.1 Therapy

In one form, the present technology comprises a method for treating a respiratory disorder comprising the step of applying positive pressure to the entrance of the airways of a patient 1000.

8.2 Treatment Systems

In one form, the present technology comprises apparatus for treating a respiratory disorder. The apparatus may comprise a PAP device 4000 for supplying pressurised air to the patient 1000 via an air delivery tube leading to a patient interface 3000.

8.3 Patient Interface 3000

A non-invasive patient interface 3000 in accordance with one aspect of the present technology comprises the following functional aspects: a seal-forming structure 3100, a plenum chamber 3200, a positioning and stabilising structure 3300 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

8.4 PAP Device 4000

It should be understood that the PAP device 4000 is described below as but one form of a respiratory apparatus. Furthermore, one skilled in the art would understand that aspects of the present technology may be applicable to other forms of respiratory apparatus such as ventilators.

A PAP device 4000 in accordance with one aspect of the present technology comprises mechanical and pneumatic components 4100, electrical components 4200 and is programmed to execute one or more algorithms 4300. The PAP device 4000 preferably has an external housing 4010, preferably formed in two parts, an upper portion 4012 of the external housing 4010, and a lower portion 4014 of the external housing 4010. In alternative forms, the external housing 4010 may include one or more panel(s) 4015. In one form, the PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 preferably comprises an inlet air filter 4112, an inlet muffler 4122, a controllable pressure device 4140 capable of supplying air at positive pressure (preferably a blower 4142), and an outlet muffler 4124. One or more sensors or transducers 4270 are included in the pneumatic path.

The preferred pneumatic block 4020 comprises a portion of the pneumatic path that is located within the external housing 4010.

The PAP device 4000 preferably has an electrical power supply 4210, one or more input devices 4220, a central controller 4230, a therapy device controller 4240, a therapy device 4245, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

8.4.1 PAP Device Mechanical & Pneumatic Components 4100

8.4.1.1 Air Filter(s) 4110

A PAP device in accordance with one form of the present technology may include an air filter 4110, or a plurality of air filters 4110.

In one form, an inlet air filter 4112 is located at the beginning of the pneumatic path upstream of a pressure device 4140.

In one form, an outlet air filter 4114, for example an antibacterial filter, is located between an outlet of the pneumatic block 4020 and a patient interface 3000.

8.4.1.2 Muffler(s) 4120

In one form of the present technology, an inlet muffler 4122 is located in the pneumatic path upstream of a pressure device 4140.

In one form of the present technology, an outlet muffler 4124 is located in the pneumatic path between the pressure device 4140 and a patient interface 3000.

8.4.1.3 Pressure Device 4140

In a preferred form of the present technology, a pressure device 4140 for producing a flow of air at positive pressure is a controllable blower 4142. For example the blower may include a brushless DC motor 4144 with one or more impellers housed in a volute. The blower may be preferably capable of delivering a supply of air, for example about 120 litres/minute, at a positive pressure in a range from about 4 cm $H_2O$ to about 20 cm $H_2O$, or in other forms up to about 30 cm $H_2O$.

The pressure device 4140 is under the control of the therapy device controller 4240.

8.4.1.4 Transducer(s) 4270

In one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

8.4.1.5 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

8.4.1.6 Air Circuit 4170

An air circuit 4170 in accordance with an aspect of the present technology is constructed and arranged to allow a flow of air between the pneumatic block 4020 and the patient interface 3000.

8.4.1.7 Oxygen Delivery 4180

In one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

8.4.2 PAP Device Electrical Components 4200

8.4.2.1 Power Supply 4210

In one form of the present technology power supply 4210 is internal of the external housing 4010 of the PAP device 4000. In another form of the present technology, power supply 4210 is external of the external housing 4010 of the PAP device 4000.

In one form of the present technology power supply 4210 provides electrical power to the PAP device 4000 only. In another form of the present technology, power supply 4210 provides electrical power to both PAP device 4000 and humidifier 5000.

8.4.2.2 Input Devices 4220

In one form of the present technology, a PAP device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

8.4.2.3 Central Controller 4230

In one form of the present technology, the central controller 4230 is a processor suitable to control a PAP device 4000 such as an x86 INTEL processor.

A processor 4230 suitable to control a PAP device 4000 in accordance with another form of the present technology includes a processor based on ARM Cortex-M processor from ARM Holdings. For example, an STM32 series microcontroller from ST MICROELECTRONICS may be used.

Another processor 4230 suitable to control a PAP device 4000 in accordance with a further alternative form of the present technology includes a member selected from the family ARM9-based 32-bit RISC CPUs. For example, an STR9 series microcontroller from ST MICROELECTRONICS may be used.

In certain alternative forms of the present technology, a 16-bit RISC CPU may be used as the processor 4230 for the PAP device 4000. For example a processor from the MSP430 family of microcontrollers, manufactured by TEXAS INSTRUMENTS, may be used.

The processor 4230 is configured to receive input signal(s) from one or more transducers 4270, and one or more input devices 4220.

The processor 4230 is configured to provide output signal(s) to one or more of an output device 4290, a therapy device controller 4240, a data communication interface 4280, a heater 5240 and a humidity controller 5250.

In some forms of the present technology, the processor 4230, or multiple such processors, is configured to implement the one or more methodologies described herein such as the one or more algorithms 4300 expressed as computer programs stored in a non-transitory computer readable storage medium, such as memory 4260. In some cases, as previously discussed, such processor(s) may be integrated with a PAP device 4000. However, in some forms of the present technology the processor(s) may be implemented discretely from the pneumatic components of the PAP device 4000, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

The central controller or processor 4230 of the PAP device 4000 is programmed to execute one or more algorithm modules 4300, preferably including a pre-processing module 4310, a therapy engine module 4320, a therapy control module 4330, and a fault condition module 4340.

8.4.2.4 Clock 4232

Preferably PAP device 4000 includes a clock 4232 that is connected to processor 4230.

8.4.2.5 Therapy Device Controller 4240

In one form of the present technology, the therapy device controller 4240 is configured to control the therapy device 4245 to deliver therapy to a patient 1000.

In one form of the present technology, therapy device controller 4240 is a therapy control module 4330 that forms part of the algorithms 4300 executed by the processor 4230.

In one form of the present technology, therapy device controller 4240 is a dedicated motor control integrated circuit. For example, in one form a MC33035 brushless DC motor controller, manufactured by ONSEMI is used.

8.4.2.6 Therapy Device 4245

In one form of the present technology, the therapy device 4245 is configured to deliver therapy to a patient 1000 under the control of the therapy device controller 4240.

Preferably the therapy device 4245 is a pressure device 4140.

8.4.2.7 Protection Circuits 4250

Preferably a PAP device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

8.4.2.8 Memory 4260

In accordance with one form of the present technology the PAP device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, PAP device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

8.4.2.9 Transducers 4270

Transducers may be internal of the device 4000, or external of the PAP device 4000. External transducers may be located for example on or form part of the air delivery circuit 4170, e.g. at the patient interface 3000. External transducers may be in the form of non-contact sensors such as a Doppler radar movement sensor that transmit or transfer data to the PAP device 4000.

8.4.2.9.1 Flow 4274

A flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In one example, a signal representing total flow Qt from the flow transducer 4274 is received by the processor 4230.

8.4.2.9.2 Pressure 4272

A pressure transducer 4272 in accordance with the present technology is located in fluid communication with the pneumatic path. An example of a suitable pressure transducer 4272 is a sensor from the HONEYWELL ASDX series. An alternative suitable pressure transducer is a sensor from the NPA Series from GENERAL ELECTRIC.

In use, a signal from the pressure transducer 4272 is received by the processor 4230. In one form, the signal from the pressure transducer 4272 is filtered prior to being received by the processor 4230.

8.4.2.9.3 Motor Speed 4276

In one form of the present technology a motor speed signal 4276 is generated. A motor speed signal 4276 is preferably provided by therapy device controller 4240. Motor speed may, for example, be generated by a speed sensor, such as a Hall effect sensor.

8.4.2.10 Data Communication Systems 4280

In one preferred form of the present technology, a data communication interface 4280 is provided, and is connected to processor 4230. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor 4230. In another form, data communication interface 4280 is an integrated circuit that is separate from processor 4230.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

8.4.2.11 Output Devices Including Optional Display, Alarms 4290

An output device 4290 in accordance with the present technology may take the form of one or more of a visual, audio and haptic unit. A visual display may be a Liquid Crystal Display (LCD) or Light Emitting Diode (LED) display.

8.4.2.11.1 Display Driver 4292

A display driver 4292 receives as an input the characters, symbols, or images intended for display on the display 4294, and converts them to commands that cause the display 4294 to display those characters, symbols, or images.

8.4.2.11.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

8.4.3 PAP Device Algorithms 4300

8.4.3.1 Pre-Processing Module 4310

A pre-processing module 4310 in accordance with the present technology receives as an input, raw data from a transducer, for example a flow or pressure transducer, and preferably performs one or more process steps to calculate one or more output values that will be used as an input to another module, for example a therapy engine module 4320.

In one form of the present technology, the output values include the interface or mask pressure Pm, the respiratory flow Qr, and the leak flow Ql.

In various forms of the present technology, the pre-processing module 4310 comprises one or more of the following algorithms: pressure compensation 4312, vent flow 4314, leak flow 4316, and respiratory flow 4318.

8.4.3.1.1 Pressure Compensation 4312

In one form of the present technology, a pressure compensation algorithm 4312 receives as an input a signal indicative of the pressure in the pneumatic path proximal to an outlet of the pneumatic block 4020. The pressure compensation algorithm 4312 estimates the pressure drop in the air circuit 4170 and provides as an output an estimated pressure, Pm, in the patient interface 3000.

8.4.3.1.2 Vent Flow 4314

In one form of the present technology, a vent flow calculation algorithm 4314 receives as an input an estimated pressure, Pm, in the patient interface 3000 and estimates a vent flow of air, Qv, from a vent 3400 in a patient interface 3000.

8.4.3.1.3 Leak Flow 4316

In one form of the present technology, a leak flow algorithm 4316 receives as an input a total flow, Qt, and a vent flow Qv, and provides as an output a leak flow Ql by calculating an average of Qt−Qv over a period sufficiently long to include several breathing cycles, e.g. about 10 seconds.

In one form, the leak flow algorithm 4316 receives as an input a total flow, Qt, a vent flow Qv, and an estimated pressure, Pm, in the patient interface 3000, and provides as an output a leak flow Ql by calculating a leak conductance, and determining a leak flow Ql to be a function of leak conductance and mask pressure Pm. Preferably leak conductance is calculated as the quotient of low pass filtered non-vent flow Qt−Qv, and low pass filtered square root of mask pressure Pm, where the low pass filter time constant has a value sufficiently long to include several breathing cycles, e.g. about 10 second.

8.4.3.1.4 Respiratory Flow 4318

In one form of the present technology, a respiratory flow algorithm 4318 receives as an input a total flow, Qt, a vent flow, Qv, and a leak flow, Ql, and estimates a respiratory flow of air, Qr, to the patient, by subtracting the vent flow Qv and the leak flow Ql from the total flow Qt.

8.4.3.2 Therapy Engine Module 4320

In one form of the present technology, a therapy engine module 4320 receives as inputs one or more of a pressure, Pm, in a patient interface 3000, and a respiratory flow of air to a patient, Qr, and provides as an output one or more therapy parameters.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, and therapy parameter determination 4328.

8.4.3.2.1 Phase Determination 4321

In one form of the present technology, a phase determination algorithm 4321 receives as an input a signal indicative of respiratory flow, Qr, and provides as an output a phase of a breathing cycle of a patient 1000.

In one form, the phase output is a discrete variable with values of either inhalation or exhalation. In one implementation of this form, the phase output is determined to have a discrete value of inhalation when a respiratory flow Qr has a positive value that exceeds a positive threshold, and the phase is determined to have a discrete value of exhalation when a respiratory flow Qr has a value that is more negative than a negative threshold.

In one form, the phase output is a discrete variable with values of one of inhalation, mid-inspiratory pause, and exhalation.

In one form, the phase output is a continuous variable, for example varying from 0 to 1, or 0 to $2\pi$ radians.

8.4.3.2.2 Waveform Determination 4322

In one form of the present technology, a control module 4330 controls a therapy device 4245 to provide an approximately constant positive airway pressure throughout a respiratory cycle of a patient.

In one form of the present technology, a control module 4330 controls a therapy device 4245 to provide positive airway pressure according to a predetermined waveform of pressure vs phase. In one form, the waveform is maintained at an approximately constant level for all values of phase. In one form, the waveform is a square wave, having a higher value for some values of phase, and a lower level for other values of phase.

In one form of the present technology a waveform determination algorithm 4322 receives as an input a value indicative of current patient ventilation, Vent, and provides as an output a waveform of pressure vs. phase.

8.4.3.2.3 Ventilation Determination 4323

In one form of the present technology, a ventilation determination algorithm 4323 receives an input a respiratory flow Qr, and determines a measure indicative of patient ventilation, Vent.

In one form ventilation determination algorithm 4323 determines a current value of patient ventilation, Vent, as half the low-pass filtered absolute value of respiratory flow, Qr.

8.4.3.2.4 Determination of Inspiratory Flow Limitation 4324

In one form of the present technology, a processor executes one or more algorithms 4324 for the detection of inspiratory flow limitation.

In one form the algorithm 4324 receives as an input a respiratory flow signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow-time curve for each breath. The curve described by the points is then scaled by a scaler to have unity length (duration/period) and unity area to remove the effects of changing respiratory rate and depth. The scaled breaths are then compared in a comparator with a pre-stored template representing a normal unobstructed breath, similar to the inspiratory portion of the breath shown in FIG. 6a. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by processor 4230 for the preceding several inspiratory events. This is repeated over the same inspiratory events for the second such point, and so on. Thus, for example, sixty five scaled data points are generated by processor 4230, and represent a moving average of the preceding several inspiratory events, e.g. three events. The moving average of continuously updated values of the (e.g. sixty five) points are hereinafter called the "scaled flow", designated as Qs(t). Alternatively, a single inspiratory event can be utilised rather than a moving average.

From the scaled flow, two shape factors relating to the determination of partial obstruction may be calculated.

Shape factor 1 is the ratio of the mean of the middle (e.g. thirty-two) scaled flow points to the mean overall (e.g. sixty-five) scaled flow points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical user.

Shape factor 2 is calculated as the RMS deviation from unit scaled flow, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can other than those described.

8.4.3.2.5 Determination of Apneas and Hypopneas 4325

In one form of the present technology, a processor 4230 executes one or more algorithms 4325 for the determination of the presence of apneas and/or hypopneas.

Preferably the one or more algorithms 4325 receive as an input a respiratory flow signal Qr and provide as an output a flag that indicates that an apnea or a hypopnea has been detected.

In one form, an apnea will be said to have been detected when a function of respiratory flow Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

In one form, a hypopnea will be said to have been detected when a function of respiratory flow Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

8.4.3.2.6 Determination of Snore 4326

In one form of the present technology, a processor 4230 executes one or more snore algorithms 4326 for the detection of snore.

In one form the snore algorithm 4326 receives as an input a respiratory flow signal Qr and provides as an output a metric of the extent to which snoring is present.

Preferably the algorithm 4326 comprises the step of determining the intensity of the flow signal in the range of 30-300 Hz. Further preferably, algorithm 4326 comprises a step of filtering the respiratory flow signal Qr to reduce background noise, e.g. the sound of airflow in the system from the blower.

8.4.3.2.7 Determination of Airway Patency 4327

In one form of the present technology, a processor 4230 executes one or more algorithms 4327 for the determination of airway patency.

In one form, airway patency algorithm 4327 receives as an input a respiratory flow signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cm $H_2O$.

In one form, airway patency algorithm 4327 receives as an input a respiratory flow signal Qr, and determines the presence or absence of a cardiogenic signal. The absence of a cardiogenic signal is taken to be an indication of a closed airway.

8.4.3.2.8 Determination of Therapy Parameters 4328

In one form of the present technology, processor 4230 executes one or more algorithms 4328 for the determination of one or more therapy parameters using the values returned by one or more of the other algorithms in the therapy engine module 4320.

In one form of the present technology, the therapy parameter is an instantaneous treatment pressure Pt. In one implementation of this form, the treatment pressure Pt is given by $$Pt = AP(\Phi) + P_0 \quad (1)$$

where:
A is the pressure support,
$P(\Phi)$ is the waveform value (in the range 0 to 1) at the current value $\Phi$ of phase, and
$P_0$ is a base pressure.

Treatment pressure Pt determined according to equation (1) may be defined as "therapeutic pressure". Various therapy modes may be defined depending on the values of the parameters A and $P_0$. In some implementations of this form of the present technology, the pressure support A is identically zero, so the treatment pressure Pt is identically equal to the base pressure $P_0$ throughout the respiratory cycle. Such implementations are generally grouped under the heading of CPAP therapy.

The base pressure $P_0$ may be a constant value that is prescribed and/or manually entered to the PAP device 4000. This alternative is sometimes referred to as constant CPAP therapy. Alternatively, the base pressure $P_0$ may be continuously computed as a function of indices or measures of one or more of sleep disordered breathing events such as flow limitation, apnea, hypopnea, patency, and snore returned by the respective algorithms in the therapy engine module 4320. This alternative is sometimes referred to as APAP therapy.

FIG. 4e is a flow chart illustrating a method 4500 carried out by the processor 4230 to continuously compute the base pressure $P_0$ as part of an APAP therapy implementation of the algorithm 4328. In such an implementation, by equation (1) the treatment pressure Pt is identically equal to the base pressure $P_0$.

The method 4500 starts at step 4520, at which the processor 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the processor 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the processor 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the processor 4230 increases the base pressure $P_0$ by a predetermined pressure increment $\Delta P$, such that the resulting treatment pressure Pt is no greater than an upper APAP pressure limit Pupper that may be set to a prescribed maximum treatment pressure Pmax. In one implementation, the predetermined pressure increment $\Delta P$ and maximum treatment pressure Pmax are 1 cm $H_2O$ and 25 cm $H_2O$ respectively. In other implementations, the pressure increment $\Delta P$ can be as low as 0.1 cm $H_2O$ and as high as 3 cm $H_2O$, or as low as 0.5 cm $H_2O$ and as high as 2 cm $H_2O$. In other implementations, the maximum treatment pressure Pmax can be as low as 15 cm $H_2O$ and as high as 35 cm $H_2O$, or as low as 20 cm $H_2O$ and as high as 30 cm $H_2O$. The method 4500 then returns to step 4520.

At step 4560, the processor 4230 decreases the base pressure $P_0$ by a decrement, such that the resulting treatment pressure Pt is no lower than a lower APAP pressure limit Plower that may be set to a prescribed minimum therapeutic pressure Pmin. The method 4500 then returns to step 4520. In one implementation, the decrement is proportional to the value of Pt−Pmin, so that the decrease of Pt to the minimum therapeutic pressure Pmin in the absence of any detected events is exponential. In one implementation, the constant of proportionality is set such that the time constant $\tau$ of the exponential decrease of Pt is 60 minutes, and the minimum therapeutic pressure Pmin is 4 cm $H_2O$. In other implementations, the time constant $\tau$ could be as low as 1 minute and as high as 300 minutes, or as low as 5 minutes and as high as 180 minutes. In other implementations, the minimum therapeutic pressure Pmin can be as low as 0 cm $H_2O$ and as high as 8 cm $H_2O$, or as low as 2 cm $H_2O$ and as 6 cm H$_2$O. Alternatively, the decrement in the base pressure P$_0$ could be predetermined, so the decrease in Pt to the minimum therapeutic pressure Pmin in the absence of any detected events is linear.

In one form of the present technology, the predetermined pressure increment ΔP is smaller, and the time constant τ is longer, than in previous implementations of the algorithm 4328. These differences, combined with the fact that the measures of flow limitation, apnea, hypopnea, patency, and snore are assessed on a single breath rather than over multiple breaths, combine to give the control loop implemented by method 4500 in this form of the present technology a smoother, less "aggressive" character than previous implementations of the algorithm 4328.

8.4.3.2.9 Initial Phase of Operation

The above described therapy modes are designed to be delivered to a sleeping patient 1000. However, if the patient 1000 is the party initiating therapy, the patient 1000 is generally awake. If the PAP device 4000 begins to deliver therapeutic pressures as described above as soon as the patient 1000 initiates treatment (such as when the patient first goes to bed at night or returns to therapy after a break in sleep in middle of the night), the patient 1000 may find that the treatment pressure Pt, even if initialised to the minimum therapeutic pressure Pmin, may be too high for them to fall asleep, or the rate of increase of pressure may be too high for the patient to comfortably fall asleep, so a purpose of therapy may be defeated.

Consequently there is a need for a "pre-sleep mode" of operation of the PAP device 4000 that may be implemented with one or more processors, such as the central controller or processor 4230. The pre-sleep mode can be invoked when the patient 1000 initiates treatment and ends at a suitable time, such as when the patient 1000 is deemed by the PAP device 4000 to have fallen asleep, and/or after a predetermined time limit has elapsed. A purpose of the pre-sleep mode of operation is to allow the patient 1000 to fall asleep with low or more comfortable pressure(s), since therapy is not required while the patient 1000 is awake. Additionally, or alternatively, the pre-sleep mode may gradually increase a pressure provided to the patient, in order to improve the chance that the patient would be comfortable with the treatment. The delivered pressure during the pre-sleep mode may be sub-therapeutic, and may follow a pre-sleep profile of pressure vs time, starting at a pre-sleep pressure Ps that may be lower or even substantially lower than the minimum therapeutic pressure Pmin. The pre-sleep profile is chosen to be compatible with the patient falling asleep. The delivered pressure may therefore start at pre-sleep pressure Ps, which may be in the range 2 to 6 cm H$_2$O, or 3 to 5 cm H$_2$O, preferably at or around 4 cm H$_2$O. The pressure may then gradually increase, such as by a ramp (e.g., continuous increase or gradual stepping of pressure) over a particular period of time toward the treatment pressure Pt, such as to the minimum therapeutic pressure, Pmin, such as 10 cm H$_2$O or more or less or other prescribed/titrated therapeutic treatment pressure that may be sufficient to prevent events of sleep disordered breathing. This particular time period over which the pressure changes from the pre-sleep pressure Ps to the predetermined minimum therapeutic pressure or other prescribed/titrated therapeutic treatment pressure as discussed herein may be considered a "ramp time". As described in more detail herein, the ramp time may be an adapted or dynamic parameter that may be determined by any of the methodologies described in more detail herein. After the pre-sleep mode has ended (i.e., at the end of the ramp time), the PAP device 4000 may transition into a therapy mode, such a mode where therapeutic pressure is fixed (e.g., a fixed CPAP or a fixed Bi-level pressure treatment) or adjusted (e.g., automatically titrated in response to detected events of sleep disordered breathing). In some implementations, the transition from pre-sleep mode to therapy mode may include a period of time wherein pressure is further increased to reach a predetermined therapeutic pressure, such as by implementation of a bridging period as disclosed in PCT Application No. PCT/AU2014/000208 to ResMed Limited, titled "Method and apparatus for treatment of respiratory disorders," the entire disclosure of which is incorporated herein by reference. Where the words 'ramp' or 'ramp time' are used, it will be understood that such references are used to generally refer to increases in pressure or the length of time of said increase in the pre-sleep mode. For example, a ramp may comprise a series of discontinuous pressure increases, as shown in FIG. 4H.

FIG. 4f is a state diagram illustrating an initial phase of operation 4600 of the therapy engine module 4320 in one form of the present technology. According to the initial phase of operation 4600, the PAP device 4000 enters the pre-sleep mode 4610 when the patient 1000 initiates treatment. In one implementation, an initiation signal is generated, namely a Treatment-On signal input to the PAP device 4000 by the patient 1000 via the input devices 4220. In another implementation, the initiation signal is a SmartStart signal generated by the processor 4230 in response to detection by the ventilation determination algorithm 4323 that the patient 1000 has started wearing the patient interface 3000, and/or is breathing. Such detection may be made by the processor 4230 in conventional fashion, for example as disclosed in European patent application no. EP 661071 to ResMed Limited, titled "Device for Continuous Positive Airway Pressure Breathing (CPAP)". During the pre-sleep mode 4610, the processor 4230 initialises the delivered pressure to the pre-sleep pressure Ps. The processor 4230 then controls the delivered pressure according to the pre-sleep profile.

The timing of the pre-sleep pressure profile during the pre-sleep mode is significant not only in allowing lower pressure to promote sleep onset but also in ensuring that sufficient therapeutic pressure to preserve sleep is delivered during sleep such as at sleep onset. Reaching the predetermined minimum therapeutic pressure too quickly may cause discomfort to the patient and prevent the patient from falling asleep. Reaching the predetermined minimum therapeutic pressure and/or transitioning to therapy mode too late may cause disruption to the patient's sleep due to untreated events of the patient's respiratory disorder(s).

Therefore, the PAP device 4000 may be configured to transition from the pre-sleep mode 4610 to therapy mode 4630 when a timer reaches a pre-sleep limit 4620. The pre-sleep limit therefore is functionally the ramp time. The pre-sleep limit may be, or may be a function of, a pre-sleep or sleep onset parameter(s), such as a function of one or more amounts of time(s) for sleep onset to occur, where such pre-sleep or sleep onset parameters may be historical in the sense that they are not, at least in part, from information regarding a current treatment session but may be from previously treatment or sleep sessions by the particular user. The pre-sleep limit may be set based on the pre-sleep parameter. Pre-sleep parameters may include sleep onset time or other similar parameter indicative of time(s) that it takes a person to transition to sleep from wakefulness, such as from previous/historical treatment sessions. Such parameters may optionally be derived/detected by sensors of a device (e.g., flow sensor, electrocardiogram, electroencephalogram, and/or motion sensor, etc.) such as to determine a measure of time of sleep onset. A sleep onset time may be the length of time from when a patient gets into bed, or when pressure treatment device is activated, to a time when initial sleep occurs.

To automatically determine the pre-sleep limit, one or more processors may collect information regarding the pre-sleep parameters of a patient, such as sleep onset times. In some implementations, the processor 4230 of the PAP device 4000 may measure sleep onset times as the length of time between when the PAP device starts providing pressure to the patient to when sleep onset is detected. Sleep onset may be detected using the PAP device 4000. For example, sleep onset may be detected/measured by any of the methods described in PCT/AU2010/000894, the entire disclosure of which is incorporated herein by reference. By way of further example, such as during the pre-sleep mode 4610, the processor 4230 of the PAP device 4000 may monitor the respiratory flow Qr or other sensor signal to detect sleep onset. Sleep onset may be detected by any conventional method of real-time sleep state determination such as by detection and analysis of biometric parameters such as respiratory and/or cardia parameters. In one implementation, sleep onset is detected if one or both of the following conditions occur:

Multiple occurrences of SDB events, such as flow limitation, apnea, hypopnea, or snore, as determined from the measures of these quantities obtained as described above, within a first predetermined interval. For example, three or more obstructive apnea or hypopnea events within a two minute interval; or five instances of snore within a 5-breath interval.

Few or no respiratory disturbances for a second predetermined interval. The second predetermined interval may be in the range 10 to 50 breaths, or 20 to 40 breaths, or 25 to 35 breaths, or from 1 to 10 minutes, 1 to 5 minutes, or 2, 3, 4, 5, 6, 7, 8 or 9 minutes, or some other time limit. To detect no respiratory disturbances, the processor 4230 tests for lack of variation over the second predetermined interval of one or more of the following respiratory variables:

Tidal volume;
Inspiratory time;
Respiratory rate;
Inspiratory peak flow;
Expiratory peak flow location;
Time since last breath.

Additionally or alternatively, pre-sleep parameters, such as sleep onset times, may be input to the device by a user. Such input may be requested or prompted, such as by a user interface, by the one or more processors, such as processor 4230, and received at the one or more input devices 4220 of the PAP device 4000. Measured and/or received sleep onset times may be stored in a memory, such as memory 4260.

The pre-sleep limit 4620 may then be determined as a function of the collected (e.g., detected/measured and/or input) information for the patient. For example, the pre-sleep limit 4620 may be calculated by the PAP device such as by setting the pre-sleep limit based on a maximum, a mean, or a percentile of the collected sleep onset times. The particular function by which the pre-sleep limit is determined/calculated by the PAP device may be pre-set (e.g., a default or fixed function) on the PAP device or may be selected by a user and/or clinician. As an example, over the course of 20 days, 20 measured sleep onset times may be collected, as shown in Table 1 below:

TABLE 1

| Day | Measured sleep onset time (min) |
|---|---|
| 1 | 15 |
| 2 | 16 |
| 3 | 16 |
| 4 | 20 |
| 5 | 24 |
| 6 | 18 |
| 7 | 19 |
| 8 | 18 |
| 9 | 17 |
| 10 | 16 |
| 11 | 10 |
| 12 | 15 |
| 13 | 14 |
| 14 | 17 |
| 15 | 12 |
| 16 | 13 |
| 17 | 14 |
| 18 | 15 |
| 19 | 18 |
| 20 | 19 |

Although the illustrative time values shown here are in minutes, it will be understood that other time units may serve as the pre-sleep limit, such as number of hours, number of seconds, number of detected breaths, etc.

For the collected values in Table 1, if using a maximum of the collected sleep onset times as the pre-sleep limit, the pre-sleep limit is calculated by the device and set to be 24 minutes. If using a mean of the collected sleep onset times as the pre-sleep limit, the pre-sleep limit is calculated by the device and set to be 16.3 minutes. If using a $90^{th}$ percentile of the collected sleep onset times as the pre-sleep limit, the pre-sleep limit is calculated by the device and set to be 20 minutes.

In some versions, the pre-sleep limit may alternatively be a further function of the determined percentile time, such as 150%, 125%, 100% or 90% of the $70^{th}$, $80^{th}$, $90^{th}$ or $100^{th}$ (i.e. maximum) percentile time. For the collected values in Table 1, if the pre-sleep limit is set as 125% of the $90^{th}$ percentile time, the pre-sleep limit is calculated by the device to be 25. As new information is collected, the time limit may be updated dynamically or at discrete intervals indicated by a user or by the device so as to permit an adaptation to a patient's sleeping pattern. Alternatively, the pre-sleep limit may be set to the most recent single collected sleep onset time (e.g., one determined from the previous treatment session).

In some implementations, the pre-sleep limit may be based on information that is collected within a timeframe, or window of time. The pre-sleep limit may be determined dynamically based on the timeframe, which may be a rolling window/timeframe, for example based on previous 5, 10 or 15 days of sleep data. Thus, in such an example, the device may collect data during a number of treatment sessions (e.g., days) of the particular time window and then set the pre-sleep limit for the next treatment session at the conclusion of the time window. Such a time window length may be a selectable parameter input to the device by a user such as by a user selecting the number of days/treatment sessions in a user interface of the device. In the case of a rolling timeframe/window, on each subsequent day/treatment session the preceding sleep onset times of the window are used (e.g., by use of a last in, first out buffer of sleep onset times with a buffer length equal to the window). In some cases, the pre-sleep limit may be calculated from the preceding timeframe/window and only be recalculated and the conclusion of re-collection of the full window such as by resetting the pre-sleep limit once every five days in the case of a five day window, etc.

For example, a pre-sleep limit set based on sleep onset times collected in a previous 10 day window, for example, may collect the first 10 sleep onset times in Table 1. As such, on day 11, if the pre-sleep limit is determined as a maximum of the collected sleep onset times in the timeframe, the pre-sleep limit is calculated by the device and set to be 24 minutes. In the case of the rolling window, on day 16, the timeframe used to determine the pre-sleep limit is shifted from day 6 to day 15 so that the pre-sleep limit is set to 19 minutes, which is the maximum for the updated timeframe.

Optionally, the time limit of the window may be calibrated, such as based on the user input. In this regard, a user's selection of such a calibration event would reset the sleep information associated with the window so that the window would then begin collecting the sleep information for the window time frame (e.g., 5, 10 or 15 days/treatment sessions etc.).

When the device is unable to calculate a pre-sleep limit due to the absence or insufficient amount of collected sleep onset time, such as for new device or a new patient, a default pre-sleep limit may be set on the PAP device. The default pre-sleep limit may be, for example, set or chosen by a user or may be a factory setting. In other implementations, the default pre-sleep limit may be based on an average sleep onset time for a person in the patient's demographic.

In some implementations, the one or more processors, such as of the PAP device, may provide for display a prompt to a user with potential pre-sleep parameters for selection. As such, the user can view data related to, for example, measured lengths of time taken for the patient to go to sleep from previously sessions, and then select the pre-sleep limit. The data displayed for the user may include one or more collected sleep onset times and/or one or more statistics of the collected sleep onset times. For example, based on the collected sleep onset times in Table 1, the prompt provided to the user may display a message as follows: "It looks like you are typically (90% of the time) falling asleep within 20 minutes of operation. Would you like to set your ramp time to 20 minutes?" In other implementations, a plurality of options may be presented on the display based on different functions (percentiles, means, etc.) of the collected information for the sleep onset times as previously described, and a user may then select an option from the plurality.

Once the pre-sleep limit is determined or selected, the one or more processors may determine a pre-sleep pressure profile that starts at a pre-sleep pressure Ps and ramps up to another pressure (e.g., a predetermined minimum therapeutic pressure Pmin) over the particularly determined/chose pre-sleep limit. The slope and/or shape of the pre-sleep profile may be determined by any conventional method known in the art. Any slope and/or shape for ramping known in the art, such as those described in PCT Application No. PCT/AU2014/000208, may be utilized by the processor 4230 of the PAP device 4000 to control pressure according to the pre-sleep profile during the pre-sleep limit.

The PAP device 4000 may deliver pressure to the patient according to the determined pre-sleep pressure profile.

FIGS. 4G and 4H depict graphs illustrating examples of the initial phase of operation 4600 of the therapy engine module 4320 of FIG. 4D as described above with reference to FIG. 4F such as in accordance with a pre-sleep limit.

In this example shown in FIG. 4G, the pre-sleep limit 4620 is determined to be 21 minutes. The solid line trace 4700 represents the delivered pressure over time, such as by ramping sub-therapeutic pressures toward treatment or therapeutic pressures over a time span representative of the pre-sleep limit. The trace 4700 during the pre-sleep mode 4610 follows a pre-sleep profile 4710, which is determined by the processor 4230 to run over the course of the pre-sleep limit 4620 of 21 minutes. The pre-sleep profile 4710 optionally comprises one increase or a series of linear increases of slope equal to 1 cm $H_2O$ per minute and duration one minute, interleaved with optional pause periods of three minutes during which the delivered pressure is constant. The slope and duration of the linear increases and the duration of the pause periods are chosen such that the delivered pressure would start at pre-sleep pressure Ps, 4 cm $H_2O$ in this example, and reach the minimum therapeutic pressure Pmin, 10 cm $H_2O$ in this example, at the pre-sleep limit time parameter of 21 minutes.

Additionally or alternatively, when sleep onset is detected prior to completion of the pre-sleep profile and during a current session with the treatment device (i.e., not an historic sleep onset for the patient), a new profile may optionally be determined for ramping the pressure from what it is when sleep onset is presently detected, to the minimum therapeutic pressure Pmin, or other treatment pressure. In some implementations, the new profile takes a shorter amount of time than the pre-sleep profile to reach the minimum therapeutic pressure Pmin so that the PAP device 4000 may start operating in therapy mode 4630 earlier than the time projected by the pre-sleep profile.

In the example shown in FIG. 4H, the pre-sleep limit is determined to be 21 minutes like the example in FIG. 4G, and the same pre-sleep profile is determined for implementation on the PAP device. In FIG. 4H, current sleep onset is detected at 14 minutes, as indicated by circle 4750, at which time a new profile 4810 that is non-historic is determined. The trace 4700 follows the new profile 4810 comprising a series of linear increases of slope equal to 1 cm $H_2O$ per minute and duration one minute, interleaved with pause periods of one minute during which the delivered pressure is constant. The slope and duration of the linear increases are the same as those of the pre-sleep profile, i.e., 1 cm $H_2O$ per minute and one minute. The duration of the pause periods is chosen to be one minute such that the delivered pressure reaches the minimum therapeutic pressure Pmin at the a further time parameter such as three minutes. As such, the minimum therapeutic pressure Pmin is reached in 17 minutes in FIG. 4H rather the determined pre-sleep limit, 21 minutes.

The features described above of the initial phase operation provide a system that can be configured to customize ramp time to a particular patient. Because the system may be configured to detect sleep onset time, unreliability with self-reporting sleep onset times might be diminished. The dynamic nature of determining the pre-sleep limit allows for adaptation to changing sleep habits of a patient, and may minimize the effect of unreliable sleep state detection. With a customized ramp time, the system may initiate and ramp up to administer treatment in a way that more suits the particular patient. As such, there may be less likelihood of disturbing or discomforting a patient as they are falling asleep or when they are sleeping, and patients may be more likely to use the system and comply with therapy.

In some cases, as previously described, sleep information (e.g., current and/or historic sleep onset parameters) is detected by a PAP device, such as with an analysis of information from a flow and/or pressure signals generated by a flow sensor and/or pressure sensor of the PAP device. For example, sleep onset may be detected by any of the methods described in PCT/AU2010/000894, the entire disclosure of which is incorporated herein by reference. However, in some versions, sleep information (e.g., historic sleep onset parameters) may be detected by other apparatus, and communicated to the PAP apparatus for setting of the sleep related pressure ramp of the pressure therapy apparatus. For example, an RF motion sensor, such as the ResMed Sensor Technologies Limited's SleepMinder sensor, may be implemented to detect and communicate sleep information, such as sleep onset or sleep onset time(s), to the PAP device for setting of the pressure ramp. Such a RF motion sensor may be, for example, any motion sensor described in PCT/EP2016/069413, PCT/US2013/051250 and/or PCT/US2014/045814, the entire disclosures of which are incorporated herein by reference.

8.5 Humidifier 5000

In one form of the present technology there is provided a humidifier 5000 comprising a water reservoir and a heating plate (not shown).

8.6 Glossary

For the purposes of the present technology disclosure, in certain forms of the present technology, one or more of the following definitions may apply. In other forms of the present technology, alternative definitions may apply.

8.6.1 General

Air: In certain forms of the present technology, air may be taken to mean atmospheric air, and in other forms of the present technology air may be taken to mean some other combination of breathable gases, e.g. atmospheric air enriched with oxygen.

Positive Airway Pressure (PAP) Therapy: The application of a supply of air to the entrance to the airways at a pressure that is continuously positive with respect to atmosphere.

Positive Airway Pressure (PAP) device: A device for providing positive airway pressure therapy.

Continuous Positive Airway Pressure (CPAP) therapy: Positive airway pressure therapy in which the treatment pressure is approximately constant through a respiratory cycle of a patient. In some forms, the pressure at the entrance to the airways will vary by a few centimetres of water within a single respiratory cycle, for example being higher during inhalation and lower during exhalation. In some forms, the pressure at the entrance to the airways will be slightly higher during exhalation, and slightly lower during inhalation.

Automatic Positive Airway Pressure (APAP) therapy: CPAP therapy in which the treatment pressure is continually adjustable between minimum and maximum limits, depending on the presence or absence of indications of SDB events.

8.6.2 Aspects of PAP Devices

Air circuit: A conduit or tube constructed and arranged in use to deliver a supply of air between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

Blower: A device that delivers a flow of air at a pressure above ambient pressure.

Controller: A device or portion of a device that adjusts an output based on an input. For example one form of controller has a variable that is under control—the control variable—that constitutes the input to the device, and a set point for the variable. The output of the device is a function of the current value of the control variable and the set point.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

8.6.3 Aspects of the Respiratory Cycle

Apnea: Preferably, apnea will be said to have occurred when flow falls below a predetermined threshold for a duration, e.g. 10 second. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate: The rate of spontaneous respiration of a patient, usually measured in breaths per minute.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: Preferably, a hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:
  (i) a 30% reduction in patient breathing for at least 10 second plus an associated 4% desaturation; or
  (ii) a reduction in patient breathing (but less than 50%) for at least 10 second, with an associated desaturation of at least 3% or an arousal.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the PAP device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including inspiratory and/or expiratory flow, per unit time. When expressed as a volume per minute, this quantity is often referred to as "minute ventilation". Minute ventilation is sometimes given simply as a volume, understood to be the volume per minute.

8.6.4 PAP Device Parameters

Flow rate: The instantaneous volume (or mass) of air delivered per unit time. While flow rate and ventilation have the same dimensions of volume or mass per unit time, flow rate is measured over a much shorter period of time. Flow rate may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow rate (sometimes referred to in shorthand as flow) will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including cm $H_2O$, g-f/cm$^2$, hectopascal. 1 cm $H_2O$ is equal to 1 g-f/cm$^2$ and is approximately 0.98 hectopascal. In this specification, unless otherwise stated, pressure is given in units of cm $H_2O$. The pressure in the patient interface is given the symbol Pm, while the treatment pressure, which represents a target value to be achieved by the mask pressure Pm at the current instant of time, is given the symbol Pt.

8.6.5 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

8.7 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

REFERENCE LABEL LIST

| | |
|---|---|
| Patient | 1000 |
| patient interface | 3000 |
| seal-forming structure | 3100 |
| plenum chamber | 3200 |
| positioning and stabilising structure | 3300 |
| Vent | 3400 |
| connection port | 3600 |
| PAP device | 4000 |
| external housing | 4010 |
| upper portion | 4012 |
| Portion | 4014 |
| Panel | 4015 |
| Chassis | 4016 |
| Handle | 4018 |
| pneumatic block | 4020 |
| pneumatic component | 4100 |
| air filter | 4110 |
| inlet air filter | 4112 |

-continued

REFERENCE LABEL LIST

| | |
|---|---|
| outlet air filter | 4114 |
| Muffler | 4120 |
| inlet muffler | 4122 |
| outlet muffler | 4124 |
| pressure device | 4140 |
| Blower | 4142 |
| brushless DC motor | 4144 |
| anti-spill back valve | 4160 |
| air circuit | 4170 |
| supplemental oxygen | 4180 |
| electrical component | 4200 |
| PCBA | 4202 |
| power supply | 4210 |
| input device | 4220 |
| central controller/processor | 4230 |
| Clock | 4232 |
| therapy device controller | 4240 |
| protection circuit | 4250 |
| Memory | 4260 |
| Transducer | 4270 |
| pressure transducer | 4272 |
| flow transducer | 4274 |
| motor speed transducer | 4276 |
| data communication interface | 4280 |
| remote external communication network | 4282 |
| local external communication network | 4284 |
| such remote external device | 4286 |
| local external device | 4288 |
| output device | 4290 |
| display driver | 4292 |
| Display | 4294 |
| Algorithm | 4300 |
| pre-processing module | 4310 |
| pressure compensation algorithm | 4312 |
| vent flow algorithm | 4314 |
| leak flow algorithm | 4316 |
| respiratory flow algorithm | 4318 |
| therapy engine module | 4320 |
| phase determination algorithm | 4321 |
| waveform determination algorithm | 4322 |
| ventilation determination algorithm | 4323 |
| inspiratory flow limitation determination algorithm | 4324 |
| apnea/hypopnea determination algorithm | 4325 |
| snore determination algorithm | 4326 |
| airway patency determination algorithm | 4327 |
| therapy parameter determination algorithm | 4328 |
| control module | 4330 |
| fault condition module | 4340 |
| Method | 4500 |
| Step | 4520 |
| Step | 4530 |
| Step | 4540 |
| Step | 4550 |
| Step | 4560 |
| initial phase of operation | 4600 |
| pre-sleep mode | 4610 |
| pre-sleep limit | 4620 |
| therapy mode | 4630 |
| trace | 4700 |
| pre-sleep profile | 4710 |
| time | 4750 |
| new profile | 4810 |
| Humidifier | 5000 |
| heater | 5240 |
| humidity controller | 5250 |

The invention claimed is:

1. An apparatus for treating a respiratory disorder comprising:
 a breathable gas pressure generating device, and
 a controller, including at least one processor, the controller configured to:
  collect historic sleep onset parameters concerning timing of a patient falling asleep;

determine, based on the historic sleep onset parameters, a pre-sleep limit as a function of a percentage of a value of a percentile of a plurality of the historic sleep onset parameters;

determine a pre-sleep profile of pressure versus time having a duration spanning the pre-sleep limit and having a plurality of ramping sub-therapeutic pressures; and control, upon initiation of treatment, setting of the breathable gas pressure generating device according to the pre-sleep profile of pressure versus time.

2. The apparatus according to claim 1, wherein the controller is configured to collect the historic sleep onset parameters by:

detecting, with one or more sensors, sleep onset of the patient during use of the breathable gas pressure generating device; and determining a length of time for the sleep onset of the patient.

3. The apparatus according to claim 1, wherein the controller is configured to collect the historic sleep onset parameters by receiving a sleep onset time at a user input device.

4. The apparatus according to claim 1, the controller is configured to collect the plurality of the historic sleep onset parameters according to a window timeframe comprising a number of treatment sessions.

5. The apparatus according to claim 4, wherein the window timeframe is a rolling window timeframe.

6. The apparatus according to claim 1, wherein the controller is further configured to set a default pre-sleep limit in an absence of a collection of the historic sleep onset parameters.

7. The apparatus according to claim 1, wherein the controller is further configured to:

control a display to provide a prompt for input, the prompt for input including: one or both of (a) at least one of the historic sleep onset parameters, and (b) at least one statistic concerning the historic sleep onset parameters; and determine the pre-sleep limit based on input received in response to the prompt.

8. The apparatus according to claim 1, wherein the pre-sleep profile starts delivered pressure at a first pressure and ends at a minimum therapeutic pressure, the minimum therapeutic pressure being higher than the first pressure.

9. A method for controlling a pressure treatment for a respiratory disorder comprising:

generating a flow of breathable gas at a pressure above atmospheric pressure with a pressure generating device, and in one or more controllers:

collecting historic sleep onset parameters concerning timing of a patient falling asleep;

determining, based on the historic sleep onset parameters, a pre-sleep limit as a function of a percentage of a value of a percentile of a plurality of the historic sleep onset parameters;

determining a pre-sleep profile of pressure versus time having a duration spanning the pre-sleep limit and having a plurality of ramping sub-therapeutic pressures; and controlling, upon initiation of treatment, setting of the flow of breathable gas according to the pre-sleep profile of pressure versus time.

10. The method according to claim 9, further comprising in the one or more controllers, collecting the historic sleep onset parameters by:

detecting, with one or more sensors, sleep onset of the patient during use of the pressure generating device; and determining a length of time for the sleep onset of the patient.

11. The method according to claim 9, wherein the collecting the historic sleep onset parameters comprises receiving a sleep onset time at a user input device.

12. The method according to claim 9, further comprising, in the one or more controllers, collecting the plurality of the historic sleep onset parameters according to a window timeframe comprising a number of treatment sessions.

13. The method according to claim 12, wherein the window timeframe is a rolling window timeframe.

14. The method according to claim 9, further comprising, in the one or more controllers, setting a default pre-sleep limit in an absence of a collection of the historic sleep onset parameters.

15. The method according to claim 9, further comprising, in the one or more controllers:

controlling a display to provide a prompt for input, the prompt for input including: one or both of (a) at least one of the historic sleep onset parameters, and (b) at least one statistic concerning the historic sleep onset parameters; and determining the pre-sleep limit based on input received in response to the prompt.

16. The method according to claim 9, wherein the pre-sleep profile starts delivered pressure at a first pressure and ends at a minimum therapeutic pressure, the minimum therapeutic pressure being higher than the first pressure.

* * * * *